US007737265B2

(12) United States Patent
Akinc et al.

(10) Patent No.: US 7,737,265 B2
(45) Date of Patent: Jun. 15, 2010

(54) RNAI MODULATION OF HIF-1 AND THERAPEUTIC USES THEREOF

(75) Inventors: Akin Akinc, Needham, MA (US); Antonin De Fougerolles, Brookline, MA (US); Hans-Peter Vornlocher, Bayreuth (DE); Philipp Hadwiger, Kulmbach (DE); Birgit Bramlage, Kulmbach (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 475 days.

(21) Appl. No.: 11/477,028

(22) Filed: Jun. 27, 2006

(65) Prior Publication Data

US 2007/0155686 A1 Jul. 5, 2007

Related U.S. Application Data

(60) Provisional application No. 60/694,382, filed on Jun. 27, 2005.

(51) Int. Cl.
C07H 21/02 (2006.01)
C07H 21/04 (2006.01)
C12Q 1/68 (2006.01)
C12P 19/34 (2006.01)
C12N 15/63 (2006.01)

(52) U.S. Cl. ............... 536/24.5; 435/6; 435/91.1; 435/455; 536/23.1; 536/24.31

(58) Field of Classification Search ............. 435/6, 435/91.1, 91.31, 455; 514/44; 536/23.1, 536/24.5, 24.31
See application file for complete search history.

(56) References Cited

U.S. PATENT DOCUMENTS

| 5,000,000 | A | * | 3/1991 | Ingram et al. ............. 435/161 |
| 5,595,760 | A | | 1/1997 | Cherif-Cheikh |
| 5,672,659 | A | | 9/1997 | Shalaby et al. |
| 5,902,880 | A | | 5/1999 | Thompson |
| 6,107,094 | A | | 8/2000 | Crooke |
| 6,146,886 | A | | 11/2000 | Thompson |
| 6,395,713 | B1 | | 5/2002 | Beigelman et al. |
| 7,217,572 | B2 | * | 5/2007 | Ward et al. ............. 435/458 |
| 2004/0180357 | A1 | * | 9/2004 | Reich et al. ............. 435/6 |
| 2005/0026164 | A1 | * | 2/2005 | Zhou ............. 435/6 |
| 2005/0107325 | A1 | | 5/2005 | Manoharan et al. |

FOREIGN PATENT DOCUMENTS

| WO | WO 94/02595 | | 2/1994 |
| WO | WO 96/10390 | | 4/1996 |
| WO | WO 96/10391 | | 4/1996 |
| WO | WO 96/10392 | | 4/1996 |
| WO | WO 00/53722 | | 9/2000 |
| WO | WO 02/44321 | * | 6/2002 |
| WO | WO 2006/038208 | * | 7/2004 |
| WO | WO 2004/064737 | | 8/2004 |
| WO | WO 2004/080406 | | 9/2004 |
| WO | WO 2004/094345 | | 11/2004 |
| WO | WO 2004/094595 | | 11/2004 |
| WO | WO2007/002718 | | 1/2007 |

OTHER PUBLICATIONS

Peracchi, A. et al., Rev. Med. Virol., vol. 14, pp. 47-64 (2004).*
Chirila, T. et al., Biomaterials, vol. 23, pp. 321-342 (2002).*
Agrawal, S. et al., Molecular Med. Today, vol. 6, pp. 72-81 (2000).*
Crooke, S. Antisense Research & Application, Chapter 1, pp. 1-50 Springer-Verlag, Publ. (S. Crooke, Ed.) (1998).*
Branch, A. Trends in Biochem. Sci., vol. 23, pp. 45-50 (1998).*
Opalinska, J.B. et al., Nature Reviews, vol. 1, pp. 503-514 (2002).*
Akhtar et al., "Cellular Uptake and Intracellular Fate of Antisense Olligonucleotides", *Trends in Cell Biology*, 2:139-144, (1992).
Aldrian-Herrada et al., "A peptide nucleic acid (PNA) is more rapidly internalized in cultured neurons when coupled to a *retro-inverso* delivery peptide. The antisense activity depresses the targed mRNA and protein in magnocellular oxytocin neurons", *Nucleic Acid Research*, 26(21): 4910-4916, (1998).
U.S. Appl. No. 60/559,917, filed May 4, 2004, Zimmermann et al.
Banai et al., "Upregulation of Vascular Endothelial Growth Factor Expression Induced by Myocardial Ischaemia: Implications for Coronary Angiogenesis", *Cardiovascular Research*, 28: 1176-1179, (1994).
Boado et al., "Anitsense Drug Delivery Throught the Blood-Brain Barrier", *Advanced Drug Delivery Reviews*, 15: 73-107, (1995).
Boado et al., "Drug Delivery of Anitsense Molecules to the Brain for Treatment of Alzheimer's Disease and Cerebrail AIDS", *Journal of Pharmaceutical Sciences*, 87(11): 1308-1315, (1998).
Couture et al., "Anti-Gene Therapy: The Use of Ribozymes to Inhibit Gene Function", *Trends in Genetics*, 12(12): 510-515 (1996).
Elbashir et al., "RNA Interference in Mediated by 21- and 22-Nucleotide RNAs", *Genes & Development*, 15: 188-200 (2001).
Fire et al., "Potent and Specific Genetic Interference by Double-Stranded RNA in *Caenorhabditis elegans*", *Nature*, 391: 806-811 (1998).
Firth et al., "Oxygen-regulated control elements in the Phosphoglycerate Kinase 1 and Lactate dehydrogenase A genes: Similarities with the erythropoietin 3' enhancer", *Proc. Natl. Acad. Sci. USA*, 91: 6496-6500, (1994).
Goldberg et al., "Regulation of Erythropoietin Gene: Evidence That the Oxygen Sensor is a Heme Protein", *Science*, 242: 1412-1415 (1988).
Goldberg et al., "Similarities between the Oxygen-sensing Mechanisms Regulating the Expression of Vascular Endothelial Growth Factor and Erythropoietin", *The Journal of Biological Chemistry*, 269(6): 4355-4359, (1994).
Gonzalez et al., "New Class of Polymers for the Delivery of Macromolecular Therapeutics", *Bioconjugate Chem.* 10: 1068-1074, (1999).
Hofland et al., "Formulation and Delivery of Nucleic Acids", *Novel Therapeutics from Modern Biotechnology*, 8: 166-172 Springer (Berlin), (1999).

(Continued)

*Primary Examiner*—Jane Zara
(74) *Attorney, Agent, or Firm*—Fenwick & West LLP

(57) ABSTRACT

The features of the present invention relate to compounds, compositions and methods useful for modulating the expression of HIF-1α, such as by the mechanism of RNA interference (RNAi). The compounds and compositions include iRNA agents that can be unmodified or chemically-modified.

27 Claims, 8 Drawing Sheets

OTHER PUBLICATIONS

Ishiwata et al., "Physical-Chemistry Characteristics and Biodistribution of Poly(ethylene glycol)-Coated Liposomes Using Poly(oxyethylene) Cholosteryl Ether", *Chemical and Pharmaceutical Bulletin*, 43(6): 1005-1011(1995).

Jelkman, W., "Erythropoietin: Structure, Control of Production, and Function", *Physcological Reviews*, 72 (2): 449-489, (1992).

Jolliet-Riant et al., "Drug Transfer Across the Blood-Brain Barrier and improvement of Brain Deliver", *Fundamental Clin. Pharmacol.* 13: 16-26, (1999).

Lasic et al., "The Stealth Liposome: A Prototypical Biomaterial", *American Chemical Society*, 95(8): 2601-2628 (1995).

Lasic et al., "Liposomes Revisted", *Science*, 267(5205): 1275-1276 (1995).

Lee et al., "Modified Liposome Formulations for Cytosolic Delivery of Macromolecules", *ACS Symposium Series*, 752: 184-192 (2000).

Limbach et al., "Summary: The Modified Nucleosides of RNA", *Nucleic Acids Research*, 22(12): 2183-2196, (1994).

Liu et al., Cationic Liposome-mediated Intravenous Gene Delivery, *The Journal of Biological Chemistry*, 270(42): 24864-24870 (1995).

Maurer et al., "Lipid-based Systems for the Intracellular Delivery of Genetic Drugs", *Molecular Membrane Biology*, 16: 129-140, (1999).

Maxwell et al., "Inducible operation of the erythropoietin 3' enhancer in multiple cell lines: Evidence for a widespread oxygen-sensing mechanism", *Proc. Natl. Acad. Sci. USA*, 90: 2423-2427 (1993).

Nykanen et al., "ATP Requirements and Small Interfering RNA Structure in the RNA Interference Pathway", *Cell*, 107: 309-321, (2001).

Oku et al., "Real-time Analysis of Liposomal Trafficking in Tumor Bearing Mice by Use of Positron Emission Tomography", *Biochimica et Biophysica Acta* 1238: 86-90 (1995).

Pardridge et al., "Vector-Medicated Delivery of a Polyamide ("Peptide") Nucleic Acid Analogue through the Blood-Brain Barrier in vivo", *Proc. Natl. Acad. Sci.* USA 92: 5592-5596 (1995).

Semenza et al., "Regulation of Erythropoietin Production", *Hematology/Oncology Clinics of North America*, 8(5): 863-884 (1994).

Semenza et al., "Transcriptional Regulation of Gene Encoding Glycolytic Enzymes by Hypoxia-Inducible Factor 1*", The Journal of Biological Chemistry, 269(38): 23757-23763 (1994).

Schweiki et al., "Vascular Endothelial Growth Factor Induced by Hypoxia May Mediate Hypoxia-Initiated Angiogenesis", *Nature*, 359: 843-845, (1992).

Tyler et al., "Peptide Nucleic Acids Targeted to the Neurotensin Receptor and Administered I.P. cross the blood-brain barrier and specifically reduce gene expression", *Proc. Natl. Acad. Sci. USA*, 96: 7053-7058 (1999).

Tyler et al., "Specific Gene Blockade Shows that Peptide Nucleic Acids Readily Enter Neuronal Cells in vivo", *FEBS Letters* 421: 280-284 (1998).

Wang et al., "General Involvement of Hypoxia-Inducible Factor 1 in Transcriptional Response to Hypoxia", *Proc. Natl. Acad. Sci. USA* 90: 4304-4308 (1993).

White et al., "Coronary Collateral Development in Swine After Coronary Artery Occlusion", *Circulation Research*, 71: 1490-1500, (1992).

Wolfe et al., "Short-Term Modulation of Glycogen Metabolism, Glycosis and Gluconeogenesis by Physiological Oxygen Concentrations in Hepatocyte Cultures", *Eur. J. Biochem.*, 135: 405-412 (1983).

* cited by examiner

TABLE 5. Data from bDNA Assay

Plate II

| see Table 1 | 1780 | 5567 | 5568 | 5569 | 5570 | 5572 | 5573 | 5574 | 5575 | VEGF |
|---|---|---|---|---|---|---|---|---|---|---|
| 1 | 22.9808192 | 41.6702692 | 47.7209737 | 16.9910351 | 22.0006855 | 81.8823786 | 18.7474115 | 64.4063368 | 22.1081231 | 86.9090693 |
| 1 | 29.3547798 | 20.8231577 | 52.8598374 | 25.6767244 | 42.710206 | 64.7257509 | 31.7159329 | 90.826336 | 18.109869 | 91.174132 |
| 1 | 29.1770184 | 22.6495691 | 10.4841939 | 6.099811174 | 8.1720738 | | 6.718693378 | 25.3204703 | 7.50489484 | 67.6085531 |
| 1 | 29.6479716 | 42.5080053 | 23.7374045 | 12.6099557 | 14.8281905 | 83.1289451 | 20.6871336 | 67.4599808 | 18.291586 | 112.051296 |
| mean | 27.79 | 31.91 | 33.70 | 15.34 | 21.93 | 76.58 | 19.47 | 62.00 | 16.50 | 89.44 |
| sd | 2.78 | 10.20 | 17.33 | 7.11 | 12.96 | 8.40 | 8.87 | 23.52 | 5.44 | 15.79 |

| | 1780 | 5576 | 5577 | 5578 | 5579 | 5580 | 5581 | 5582 | 5583 | VEGF |
|---|---|---|---|---|---|---|---|---|---|---|
| 2 | 54.7362999 | 54.7042338 | 37.7312684 | 27.229542 | 39.6760783 | 14.9313941 | 44.706462 | 29.837129 | 20.793408 | 87.2001032 |
| 2 | 43.8758965 | 65.4160402 | 44.5403078 | 68.3976675 | | 65.0044591 | | 68.8883176 | 33.5413579 | 104.744928 |
| 2 | 34.5307239 | 38.0606601 | 27.6615006 | 32.9839584 | 51.9152978 | 52.373914 | 79.4226935 | 46.241901 | 22.8622346 | 104.713627 |
| 2 | 31.4460969 | 29.2456965 | 22.4695714 | 16.9390136 | 22.7149391 | 24.6284232 | 58.2275664 | 33.7983046 | 15.4813264 | 108.345481 |
| mean | 41.15 | 46.86 | 33.10 | 36.39 | 38.10 | 39.23 | 60.79 | 44.69 | 23.17 | 101.25 |
| sd | 9.08 | 14.09 | 8.59 | 19.35 | 11.97 | 20.25 | 14.29 | 15.23 | 6.57 | 8.25 |

| | 1780 | 5584 | 5585 | 5586 | 5587 | 5588 | 5589 | 5590 | 5571 | VEGF |
|---|---|---|---|---|---|---|---|---|---|---|
| 3 | 52.8857535 | 50.8729465 | 37.5277008 | 43.2687662 | 159.505055 | 20.9208484 | 39.2654631 | 25.1865456 | 17.9824898 | 119.872598 |
| 3 | 61.2883512 | 36.1474624 | 47.1793924 | 91.2289614 | 252.256813 | 41.286679 | 59.5424204 | 12.9118937 | 24.49464 | 109.462654 |
| 3 | 59.7247375 | 60.2626887 | 34.2001026 | 60.8570521 | 269.324063 | 53.3894804 | 41.8419818 | 25.0784782 | 18.6490188 | 116.362207 |
| 3 | 37.1179749 | 30.6535122 | 20.5053397 | 35.4513158 | 97.8755456 | 22.128333 | 24.9928803 | 11.7993767 | 10.5596196 | 92.9183209 |
| mean | 52.75 | 44.48 | 34.85 | 57.70 | 194.74 | 34.43 | 41.41 | 18.74 | 17.92 | 109.65 |
| sd | 9.56 | 11.73 | 9.56 | 21.43 | 69.81 | 13.60 | 12.28 | 6.40 | 4.95 | 10.36 |

| see Table 2 | 1780 | 5591 | 5592 | 5593 | 5594 | 5595 | 5596 | 5597 | 5598 | VEGF |
|---|---|---|---|---|---|---|---|---|---|---|
| 4 | 53.4043625 | 77.7120603 | 90.8214755 | 27.3932955 | 17.4779802 | 105.769243 | 20.679967 | 103.578494 | 24.8151195 | 79.6894189 |
| 4 | 46.8964629 | 49.4449165 | 79.6927311 | 27.1501613 | 15.1713199 | 163.023583 | 22.5652457 | 100.357454 | 36.6907516 | 99.2088951 |
| 4 | 31.1985134 | 50.6978233 | 48.1519264 | 25.5729259 | 22.3463961 | 274.180707 | 27.0298787 | 126.302366 | 26.8873992 | 96.5661238 |
| 4 | 40.5314508 | 39.2638232 | 50.9552459 | 17.1809823 | 13.5432535 | 70.7156839 | 14.6567134 | 80.3706147 | 21.8210144 | 76.0163864 |
| mean | 43.01 | 54.28 | 67.41 | 24.32 | 17.13 | 153.42 | 21.23 | 102.65 | 27.55 | 87.87 |
| sd | 8.19758756 | 14.2368978 | 18.3070677 | 4.18300968 | 3.31786703 | 77.1135131 | 4.44218618 | 16.2935823 | 5.57434246 | 10.1442493 |

FIG. 3A

|   | mean 1780 | VEGF |
|---|---|---|
| 1 | 46.4675522 | 100.00 |
| 1 | 10.6884887 | 9.93911514 |
| 1 | 22.0746935 | |
| 1 | | |
| 2 | 108.115752 | |
| 2 | | 141.652115 |
| 2 | | |
| 2 | | |
| 3 | | |
| 3 | | |
| 3 | | |
| 4 | | |
| 4 | | |
| 4 | | |

FIG. 3B

|   | 1780 | 5599 | 5600 | 5601 | 5602 | 5603 | 5604 | 5605 | 5606 | VEGF |
|---|---|---|---|---|---|---|---|---|---|---|
| 5 | 46.9382078 | 53.6069696 | 130.618309 | 123.827988 | 40.9503061 | 66.0798767 | 108.943462 | 91.7848398 | 62.6070101 | 103.466295 |
| 5 | 83.1716098 | 38.6121052 | 69.2718698 | 59.2384758 | 32.9972465 | 60.7431829 | 94.7281821 | 70.8049181 | 53.4832776 | 100.227077 |
| 5 | 53.1826132 | 41.844386 | 111.277642 | 127.538472 | 32.1295773 | 76.9669925 | 113.163166 | 91.078392 | 59.8723756 | 100.011539 |
| 5 |  |  | 55.0535985 | 48.1189019 | 21.4954475 | 31.2355349 | 58.934304 | 59.825226 | 39.5228303 | 83.0246984 |
| mean | 61.10 | 44.69 | 91.56 | 89.68 | 31.89 | 58.76 | 93.94 | 78.37 | 53.87 | 96.68 |
| sd | 15.8155758 | 6.44335981 | 30.5933608 | 36.2400341 | 6.91771678 | 16.9307731 | 21.3345608 | 13.625346 | 8.92124831 | 8.00315484 |

|   | 1780 | 5607 | 5608 | 5609 | 5610 | 5611 | 5612 | 5613 | 5614 | VEGF |
|---|---|---|---|---|---|---|---|---|---|---|
| 6 | 55.0813748 | 83.7230274 | 87.8376726 | 71.7833199 | 80.2538733 | 44.6063263 | 65.1327327 | 57.2230161 | 18.1972409 | 122.862515 |
| 6 | 55.7628247 | 71.1600224 | 49.2616807 | 168.551972 | 148.088568 | 78.0146464 | 45.6274024 | 45.5512898 | 27.8883979 | 95.1823137 |
| 6 | 57.2716959 | 63.9618247 | 50.6065148 | 103.372559 | 101.210118 | 50.5485981 | 57.367451 | 41.3458639 | 15.3126911 | 114.73795 |
| 6 | 43.9182367 | 51.5422963 | 43.7386637 | 84.2272321 | 87.4144203 | 46.016526 |  | 31.1262005 | 18.7660879 | 127.643817 |
| mean | 53.01 | 67.60 | 57.86 | 106.98 | 104.24 | 54.80 | 56.04 | 43.81 | 20.04 | 115.11 |
| sd | 5.30779711 | 11.6588153 | 17.497265 | 37.2847691 | 26.4116996 | 13.5835799 | 8.01793999 | 9.35269773 | 4.71602078 | 12.3940421 |

Plate II PTO see Table 3

|   | 1780 | 5639 | 5640 | 5641 | 5642 | 5643 | 5644 | 5645 | 5646 | VEGF |
|---|---|---|---|---|---|---|---|---|---|---|
| 1 | 77.2104987 | 27.0528028 | 86.8711935 | 31.0290038 | 24.5625967 | 32.3362821 | 20.6057789 | 37.1062946 | 12.0477385 | 109.657672 |
| 1 | 43.5640263 | 17.5039897 | 42.946904 | 8.22627416 | 13.846795 | 35.3633522 | 50.7486415 | 23.2550547 | 3.7562352 | 171.850816 |
| 1 | 74.0126867 | 29.0896272 | 10.9780991 | 25.3055314 | 25.0984784 | 40.1510364 | 43.396611 | 144.299784 | 12.5076363 | 37.8408673 |
| 1 | 14.2745989 | 27.0013017 | 35.7927574 | 48.1279852 | 29.3096395 | 60.0968282 |  | 84.9690688 | 25.1773792 | 94.724797 |
| mean | 52.27 | 25.16 | 44.15 | 28.17 | 23.20 | 41.99 | 38.25 | 72.41 | 13.37 | 103.52 |
| sd | 25.56 | 4.50 | 27.37 | 14.25 | 5.71 | 10.82 | 12.83 | 47.40 | 7.65 | 47.69 |

|   | 1780 | 5647 | 5648 | 5649 | 5650 | 5651 | 5652 | 5653 | 5654 | VEGF |
|---|---|---|---|---|---|---|---|---|---|---|
| 2 | 17.3913243 | 75.1377152 | 11.0464959 | 46.775437 | 39.1564658 | 37.121919 | 46.9441315 | 48.6650848 | 56.0547467 | 68.2315311 |
| 2 | 17.9039608 | 35.9741024 | 18.8497963 | 20.6353632 | 25.4579894 | 21.951168 | 23.3441861 | 61.4070881 | 18.8777984 | 81.5043312 |
| 2 | 5.8738544 | 75.5596267 | 13.3453793 | 18.2199312 | 64.4508055 | 40.5105585 | 56.0811409 | 38.1147518 | 10.880353 | 38.9417377 |
| 2 | 12.5899344 | 53.6650704 | 10.8608128 | 34.3450481 | 15.9984672 | 71.3933719 | 46.5541789 | 89.8902765 | 49.4775312 | 73.0977325 |
| mean | 13.44 | 60.08 | 13.53 | 29.99 | 36.27 | 42.74 | 43.23 | 59.52 | 33.82 | 65.44 |
| sd | 4.84 | 16.50 | 3.23 | 11.48 | 18.24 | 17.96 | 12.10 | 19.38 | 19.29 | 16.02 |

FIG. 3C

|   |   |   | mean |   | VEGF |
|---|---|---|------|---|------|
| 5 | 117.942196 | 139.42925 | 1780 | | 100.00 |
| 5 | | | 46.9844791 | | 17.274448 |
| 5 | | | 20.5459599 | | |
| 5 | | | | | |
| 6 | 119.312112 | | | | |
| 6 | | | | | |
| 6 | | | | | |
| 6 | | | | | |
| 1 | | | | | |
| 1 | | | | | |
| 1 | | | | | |
| 1 | 94.3188118 | | | | |
| 2 | | | | | |
| 2 | | | | | |
| 2 | | | | | |
| 2 | | | | | |

FIG. 3D

| | 1780 | 5655 | 5656 | 5657 | 5658 | 5659 | 5660 | 5661 | 5662 | VEGF |
|---|---|---|---|---|---|---|---|---|---|---|
| 3 | 16.0734555 | 3.33277657 | 14.3529257 | 38.8078541 | 42.0963217 | 25.8415122 | 11.9003406 | 17.4985425 | 82.1406126 | 46.1061615 |
| 3 | 15.6792864 | 5.08548119 | 53.14304 | 52.2256331 | 44.4422064 | 57.8293951 | 47.1817785 | 56.493845 | 65.2173075 | 107.680417 |
| 3 | 56.202298 | 9.44319323 | 55.8339197 | 22.1036122 | 67.3075322 | 69.6556002 | 69.7334448 | 87.3976736 | 63.7868205 | 122.010206 |
| 3 | 60.8286734 | 49.6662653 | 25.5584854 | | 15.0055686 | 61.6003583 | 94.8947105 | 62.0846127 | 68.6549716 | 158.86782 |
| mean | 37.20 | 16.88 | 37.22 | 37.71 | 42.21 | 53.73 | 55.93 | 55.87 | 69.95 | 108.67 |
| sd | 21.38 | 19.06 | 17.74 | 12.32 | 18.54 | 16.66 | 30.51 | 25.03 | 7.26 | 40.66 |
| see Table 4 | 1780 | 5663 | 5664 | 5665 | 5666 | 5667 | 5668 | 5669 | 5670 | VEGF |
| 4 | 142.566194 | 53.5754492 | | 55.2898597 | 49.371668 | 220.556336 | 36.1088609 | | 31.9760316 | 206.532404 |
| 4 | 58.3063852 | 49.9615606 | 51.7437191 | 19.4347829 | 31.8157558 | 102.100633 | 17.5081308 | 61.442187 | 11.8123428 | 77.5825938 |
| 4 | 38.1865348 | | 35.1400781 | 39.7840944 | 48.1314996 | 102.42227 | 21.08791 | 64.7787978 | 12.8426256 | 141.415041 |
| 4 | 56.2641166 | 62.7857 | 19.8233223 | 14.5198461 | 25.8546417 | 66.2166919 | 14.7528934 | 71.0096296 | 10.8601777 | 57.5150104 |
| mean | 73.83 | 55.44 | 35.57 | 32.26 | 38.79 | 122.82 | 22.36 | 65.74 | 16.87 | 120.76 |
| sd | 40.4495485 | 5.3990479 | 13.034977 | 16.3262492 | 10.1882143 | 58.3131319 | 8.24709062 | 3.96501638 | 8.7479964 | 58.411799 |
| | 1780 | 5671 | 5672 | 5673 | 5674 | 5675 | 5676 | 5677 | 5678 | VEGF |
| 5 | 44.1529361 | 28.8558178 | 23.6596088 | 51.2561406 | 79.3140852 | 45.3020129 | 79.4868046 | 68.8720721 | 45.538058 | 75.0440264 |
| 5 | 77.6630376 | 37.1574297 | 78.1354031 | 58.8853247 | 56.7481781 | 71.1612864 | 114.952647 | 90.7961373 | 50.1984881 | 111.770692 |
| 5 | 109.535559 | | 46.4044008 | 54.8104823 | 53.4453537 | 88.1627209 | 102.711972 | 113.712265 | 67.1705957 | 127.939274 |
| 5 | 42.2662834 | 26.6628759 | 46.3762273 | 53.2195833 | 83.3287357 | 61.6022994 | 98.6817981 | 120.180373 | 63.6166853 | 113.205392 |
| mean | 68.40 | 30.89 | 48.64 | 54.54 | 68.21 | 66.56 | 98.96 | 98.39 | 56.63 | 106.99 |
| sd | 27.6081022 | 4.51985023 | 19.3915011 | 2.80545038 | 13.2405156 | 15.5268329 | 12.7389636 | 20.2396082 | 9.00435239 | 19.499381 |
| | 1780 | 5679 | 5680 | 5681 | 5682 | 1780 | 5684 | 5685 | 5686 | VEGF |
| 6 | 46.2797479 | 29.5353282 | 41.4006063 | 83.3391699 | 105.517975 | 80.2850684 | 69.2884879 | 69.6029495 | 9.61170124 | 94.4282051 |
| 6 | 48.5341409 | 38.6828352 | 50.3325689 | 49.8825374 | 107.042315 | 53.77741878 | 11.6361038 | 61.8258353 | 10.7257724 | 49.6111503 |
| 6 | 42.1662308 | 34.2637207 | 43.072731 | 56.5433833 | 119.091966 | 63.1503607 | 49.429459 | 59.2654313 | 16.4900062 | 131.852874 |
| 6 | 10.1017347 | 33.0804383 | 25.3549572 | 87.5160435 | 78.3840863 | 46.8114214 | 37.2290868 | 42.7081739 | 9.3614753 | 102.589249 |
| mean | 36.77 | 33.89 | 40.04 | 69.32 | 102.51 | 61.01 | 41.90 | 58.35 | 11.55 | 94.62 |
| sd | 15.5655549 | 3.26838996 | 9.119157789 | 16.3454123 | 14.8880077 | 12.550557 | 20.8836622 | 9.80070203 | 2.89955272 | 29.4772335 |

SEQUENCE LISTING

<160> NUMBER OF SEQ ID NOS: 192

<210> SEQ ID NO 1
<211> LENGTH: 21

```
<212> TYPE: DNA
<213> ORGANISM: Artificial Sequence
<220> FEATURE:
<223> OTHER INFORMATION: Synthetically generated oligonucleotide

<400> SEQUENCE: 1
cugauuugug aacccauuct t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 2
ucccuucaac aaacagaaut t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 3
acugcagggu gaagaauuan t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 4
acacagugug uuugauuuun t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 5
gcucccuaua ucccaauggt t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 6
uggacacagu guguuugaun t                                              21
```

```
<210> SEQ ID NO 7
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 7
ucugaucauc ugaccaaaat t                                      21

<210> SEQ ID NO 8
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 8
cagcacgacu ugauuuucun t                                      21

<210> SEQ ID NO 9
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 9
ugcaggguga agaauuacut t                                      21

<210> SEQ ID NO 10
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 10
cuggacacag uguguuugat t                                      21

<210> SEQ ID NO 11
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 11
cucccuucaa caaacagaat t                                      21

<210> SEQ ID NO 12
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 12
cugcagggug aagaauuacn t                                      21
```

<210> SEQ ID NO 13
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 13
gauggaagca cuagacaaat t                                        21

<210> SEQ ID NO 14
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 14
ugcucaucag uugccacuut t                                        21

<210> SEQ ID NO 15
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 15
gaucaguugu caccauuagt t                                        21

<210> SEQ ID NO 16
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 16
guggauaugu cuggguugat t                                        21

<210> SEQ ID NO 17
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 17
uacugcaggg ugaagaauut t                                        21

<210> SEQ ID NO 18
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 18
ccuacugcag ggugaagaat t                                        21

<210> SEQ ID NO 19
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 19
gccacuucga aguagugcut t                    21

<210> SEQ ID NO 20
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 20
agagguggau augucugggt t                    21

<210> SEQ ID NO 21
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 21
cuaacuggac acagugugt t                     21

<210> SEQ ID NO 22
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 22
agucggacag ccucaccaat t                    21

<210> SEQ ID NO 23
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 23
gagcuuugga ucaaguuaat t                    21

<210> SEQ ID NO 24
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 24
gacacagugu guuugauuun t                    21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 25
gaauggguuc acaaaucagt t                    21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 26
auucuguuug uugaagggat t                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 27
uaauucuuca cccugcagun t                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 28
aaaaucaaac acacugugun t                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 29
ccauugggau auagggagct t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 30
aucaaacaca cuguguccan t                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 31
uuuuggucag augaucagat t                                                 21

<210> SEQ ID NO 32
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 32
agaaaaucaa gucgugcugn t                                                 21

<210> SEQ ID NO 33
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 33
aguaauucuu cacccugcat t                                                 21

<210> SEQ ID NO 34
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 34
ucaaacacac uguguccagt t                                                 21

<210> SEQ ID NO 35
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 35
uucuguuugu ugaagggagt t                                                 21

<210> SEQ ID NO 36
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 36
guaauucuuc acccugcagn t                                                 21

<210> SEQ ID NO 37
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 37 uugucuagu gcuuccauct t                                                    21

<210> SEQ ID NO 38
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 38
aaguggcaac ugaugagcat t                                                   21

<210> SEQ ID NO 39
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 39
cuaaugguga caacugauct t                                                   21

<210> SEQ ID NO 40
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 40
ucaacccaga cauauccact t                                                   21

<210> SEQ ID NO 41
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 41
aauucuucac ccugcaguat t                                                   21

<210> SEQ ID NO 42
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 42
uucuucaccc ugcaguaggt t                                                   21

<210> SEQ ID NO 43
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 43
agcacuacuu cgaaguggct t                                                   21

<210> SEQ ID NO 44
<211> LENGTH: 21

```
<212> TYPE: DNA
<213> ORGANISM: Artificial Sequence
<220> FEATURE:
<223> OTHER INFORMATION: Synthetically generated oligonucleotide

<400> SEQUENCE: 44
cccagacaua uccaccucut t                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 45
acacacugug uccaguuagt t                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 46
uuggugaggc uguccgacut t                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 47
uuaacuugau ccaaagcuct t                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 48
aaaucaaaca cacugugucn t                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 7, 9, 13, 14, 15, 17, 18, 19
<223> OTHER INFORMATION: n =  2'O-methyl modification coresponding base
<220> FEATURE:
<221> NAME/KEY: misc_feature
<222> LOCATION: 20
<223> OTHER INFORMATION: n = thymidine phosphorothioate modification

<400> SEQUENCE: 49
cugauuugug aacccauucn t                                              21
```

<210> SEQ ID NO 50
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 10, 14, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 50
ucccuucaac aaacagaaun t                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 10, 17, 18
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 51
acugcagggu gaagaauuan t                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 4, 7, 9, 11, 12, 13, 16, 17, 18, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 52
acacagugug uuugauuuun t                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 4, 5, 6, 7, 9, 11, 12, 13, 14, 17
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 53
gcucccuaua ucccaauggn t                                              21

```
<210> SEQ ID NO 54
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 7, 10, 12, 14, 15, 16, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 54
uggacacagu guguuugaun t                                              21

<210> SEQ ID NO 55
<211> LENGTH: 21
<212> TYPE: DNA
<213> ORGANISM: Artificial Sequence
<220> FEATURE:
<221> NAME/KEY: modified_base
<222> LOCATION: 1, 2, 3, 6, 7, 9, 10, 11, 14, 15
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification
<220> FEATURE:
<223> OTHER INFORMATION: Synthetically generated oligonucleotide

<400> SEQUENCE: 55
ucugaucauc ugaccaaaan t                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 6, 8, 9, 10, 11, 14, 15, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 56
cagcacgacu ugauuuucun t                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 8, 15, 16, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 57
ugcaggguga agaauuacun t                                              21
```

<210> SEQ ID NO 58
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 6, 8, 11, 13, 15, 16, 17
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 58
cuggacacag uguguuugan t                                           21

<210> SEQ ID NO 59
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 8, 11, 15
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 59
cucccuucaa caaacagaan t                                           21

<210> SEQ ID NO 60
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 9, 11, 16, 17, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification
<220> FEATURE:

<400> SEQUENCE: 60
cugcagggug aagaauuacn t                                           21

<210> SEQ ID NO 61
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 9, 11, 12, 16,
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 61
gauggaagca cuagacaaan t                                          21

<210> SEQ ID NO 62
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 5, 7, 8, 11, 12, 14, 15, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 62
ugcucaucag uugccacuun t                                          21

<210> SEQ ID NO 63
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 7, 8, 10, 11, 13, 14, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 63
gaucaguugu caccauuagn t                                          21

<210> SEQ ID NO 64
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 6, 8, 10, 11, 12, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 64
guggauaugu cuggguugan t                                          21

<210> SEQ ID NO 65
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 6, 11, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 65
uacugcaggg ugaagaauun t                                                 21

<210> SEQ ID NO 66
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 5, 6, 8, 13
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 66
ccuacugcag ggugaagaan t                                                 21

<210> SEQ ID NO 67
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 6, 7, 8, 13, 16, 18, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 67
gccacuucga aguagugcun t                                                 21

<210> SEQ ID NO 68
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 6, 10, 12, 14, 15, 16
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 68
agagguggau augucugggn t                                                 21

<210> SEQ ID NO 69
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 10, 12, 15, 17, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 69
cuaacuggac acagugugun t                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 8, 11, 12, 13, 14, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 70
agucggacag ccucaccaan t                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 5, 6, 7, 11, 12, 16, 17,
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 71
gagcuuugga ucaaguuaan t                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 5, 8, 10, 12, 13, 14,17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 72
gacacagugu guuugauuun t                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 8, 9, 10, 12, 16, 17
<223> OTHER INFORMATION: n =  2'O-methyl 2'-fluoro modifications
     corresponding base
<220> FEATURE:
<221> NAME/KEY: misc_feature
<222> LOCATION: 20
<223> OTHER INFORMATION: n = thymidine phosphorothioate modification

<400> SEQUENCE: 73
gaaugggnuc acaaaucagn t                                          21

<210> SEQ ID NO 74
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 4, 5, 7, 8, 9, 11, 12,
<223> OTHER INFORMATION: n = 2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 74
auucuguuug uugaagggan t                                          21

<210> SEQ ID NO 75
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 5, 6, 7, 8, 9, 11, 12, 13, 14, 16, 19
<223> OTHER INFORMATION: n = 2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 75
uaauucuuca cccugcagun t                                          21

<210> SEQ ID NO 76
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 5, 6, 10, 12, 14, 15, 17, 19
<223> OTHER INFORMATION: n = 2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 76
aaaaucaaac acacugugun t                                          21

<210> SEQ ID NO 77
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 5, 10, 12, 19
<223> OTHER INFORMATION: n = 2'O-methyl 2'-fluoro modifications
      corresponding base
<220> FEATURE:
<221> NAME/KEY: misc_feature

```
<222> LOCATION: 20
<223> OTHER INFORMATION: n = thymidine phosphorothioate modification

<400> SEQUENCE: 77
ccauugggau auagggagcn t                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 7, 9, 11, 12, 14, 16, 17, 18
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 78
aucaaacaca cuguguccan t                                              21

<210> SEQ ID NO 79
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 7, 8, 12, 15, 16
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 79
uuuuggucag augaucagan t                                              21

<210> SEQ ID NO 80
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 8, 12, 13, 15, 17, 18
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 80
agaaaaucaa gucgugcugn t                                              21

<210> SEQ ID NO 81
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 7, 8, 9, 10, 11, 13, 14, 15, 16, 18
```

```
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 81
aguaauucuu cacccugcan t                                           21

<210> SEQ ID NO 82
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 6, 8, 10, 11, 13, 15, 16, 17
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 82
ucaaacacac uguguccagn t                                           21

<210> SEQ ID NO 83
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 6, 7, 8, 10. 11
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 83
uucuguuugu ugaagggagn t                                           21

<210> SEQ ID NO 84
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 5, 6, 7, 8, 9, 10 12, 13, 14, 15, 17
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 84
guaauucuuc acccugcagn t                                           21

<210> SEQ ID NO 85
<211> LENGTH: 21
<212> TYPE: DNA
<213> ORGANISM: Artificial Sequence
<220> FEATURE:
```

```
<223> OTHER INFORMATION: Synthetically generated oligonucleotide
<220> FEATURE:
<221> NAME/KEY: modified_base
<222> LOCATION: 1, 2, 3, 5, 6, 7, 10, 12, 13, 14, 15, 16, 18, 19
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 85
uuugucuagu gcuuccaucn t                                              21

<210> SEQ ID NO 86
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 7, 10, 11, 14, 18
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 86
aaguggcaac ugaugagcan t                                              21

<210> SEQ ID NO 87
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 8, 11, 14, 15, 18, 19
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 87
cuaaugguga caacugaucn t                                              21

<210> SEQ ID NO 88
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 7, 11, 13, 15, 16, 17, 19
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 88
ucaacccaga cauauccacn t                                              21

<210> SEQ ID NO 89
```

```
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 6, 7, 8, 10, 11, 12, 13, 15, 18
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 89
aauucuucac ccugcaguan t                                             21

<210> SEQ ID NO 90
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 8, 9, 10, 11, 13, 16,
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 90
uucuucaccc ugcaguaggn t                                             21

<210> SEQ ID NO 91
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 5, 6, 8, 9, 10, 11, 16, 19
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 91
agcacuacuu cgaaguggcn t                                             21

<210> SEQ ID NO 92
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 7, 9, 11, 12, 13, 15, 16, 17, 18, 19
<223> OTHER INFORMATION: n =  2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 92
```
cccagacaua uccaccucun t    21

<210> SEQ ID NO 93
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 4, 6, 7, 9, 11, 12, 13, 16, 17
<223> OTHER INFORMATION: n = 2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 93
acacacugug uccaguuagn t    21

<210> SEQ ID NO 94
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 10, 11, 13, 14, 15, 18, 19
<223> OTHER INFORMATION: n = 2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 94
uuggugaggc uguccgacun t    21

<210> SEQ ID NO 95
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 7, 10, 11, 12, 17, 18, 19
<223> OTHER INFORMATION: n = 2'O-methyl 2'-fluoro modifications
      corresponding base
<220> FEATURE:
<221> NAME/KEY: misc_feature
<222> LOCATION: 20
<223> OTHER INFORMATION: n = thymidine phosphorothioate modification

<400> SEQUENCE: 95
uuaacuugau ccaaagcucn t    21

<210> SEQ ID NO 96
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 5, 9, 11, 13, 14, 16, 18, 19
<223> OTHER INFORMATION: n = 2'O-methyl 2'-fluoro modifications
      corresponding base
<220> FEATURE:
<221> NAME/KEY: misc_feature
<222> LOCATION: 20

<223> OTHER INFORMATION: n = thymidine phosphorothioate modification

<400> SEQUENCE: 96
aaaucaaaca cacugugucn t         21

<210> SEQ ID NO 97
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 7, 9, 13, 14, 15, 17, 18, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 97
cugauuugug aacccauucn t         21

<210> SEQ ID NO 98
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 10, 14, 19
<223> OTHER INFORMATION: n = 2'O-methyl modifications corresponding base
<220> FEATURE:
<221> NAME/KEY: misc_feature
<222> LOCATION: 20
<223> OTHER INFORMATION: n = thymidine phosphorothioate modification

<400> SEQUENCE: 98
ucccuucaac aaacagaaun t         21

<210> SEQ ID NO 99
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 10, 17, 18
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 99
acugcagggu gaagaauuan t         21

<210> SEQ ID NO 100
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 4, 7, 9, 11, 12, 13, 16, 17, 18, 19
<223> OTHER INFORMATION: n = 2'O-methyl corresponding base
<220> FEATURE:
<221> NAME/KEY: misc_feature
<222> LOCATION: 20
<223> OTHER INFORMATION: n = thymidine phosphorothioate modification

<400> SEQUENCE: 100
acacagugug uuugauuuun t                                              21

<210> SEQ ID NO 101
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 4, 5, 6, 7, 9, 11, 12, 13, 14, 17
<223> OTHER INFORMATION: n =  2'O-methyl modifications corresponding
      base
<220> FEATURE:
<221> NAME/KEY: misc_feature
<222> LOCATION: 20
<223> OTHER INFORMATION: n = thymidine phosphorothioate modification

<400> SEQUENCE: 101
gcucccuaua ucccaauggn t                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 7, 10, 12, 14, 15, 16, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 102
uggacacagu guguuugaun t                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 6, 7, 9, 10, 11, 14, 15
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 103
ucugaucauc ugaccaaaan t                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 6, 9, 10, 11, 14, 15, 16, 17, 18, 19
<223> OTHER INFORMATION: n =  2'O-methyl modifications corresponding
      base

```
<220> FEATURE:
<221> NAME/KEY: misc_feature
<222> LOCATION: 20
<223> OTHER INFORMATION: n = thymidine phosphorothioate modification

<400> SEQUENCE: 104
cagcacgacu ugauuuucun t                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 8, 15, 16, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 105
ugcaggguga agaauuacun t                                              21

<210> SEQ ID NO 106
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 6, 8, 11, 13, 15, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 106
cuggacacag uguguuugan t                                              21

<210> SEQ ID NO 107
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 8, 11, 15
<223> OTHER INFORMATION: n =  2'O-methyl modifications corresponding
      base
<220> FEATURE:
<221> NAME/KEY: misc_feature
<222> LOCATION: 20
<223> OTHER INFORMATION: n = thymidine phosphorothioate modification

<400> SEQUENCE: 107
cucccuucaa caaacagaan t                                              21

<210> SEQ ID NO 108
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 4, 9, 16, 17, 19
```

```
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 108
cugcagggug aagaauuacn t                                              21

<210> SEQ ID NO 109
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 9, 11, 12, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 109
gauggaagca cuagacaaan t                                              21

<210> SEQ ID NO 110
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 5, 7, 8, 11, 12, 14, 15, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 110
ugcucaucag uugccacuun t                                              21

<210> SEQ ID NO 111
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 7, 8, 10, 11, 13, 14, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 111
gaucaguugu caccauuagn t                                              21

<210> SEQ ID NO 112
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 6, 8, 10, 11, 12, 16, 17
```

-continued

```
<223> OTHER INFORMATION: n =  2'O-methyl modifications corresponding
      base
<220> FEATURE:
<221> NAME/KEY: misc_feature
<222> LOCATION: 20
<223> OTHER INFORMATION: n = thymidine phosphorothioate modification

<400> SEQUENCE: 112
guggauaugu cuggguugan t                                              21

<210> SEQ ID NO 113
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 5, 6, 8, 13
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 113
uacugcaggg ugaagaauun t                                              21

<210> SEQ ID NO 114
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3 5, 6, 8, 13,
<223> OTHER INFORMATION: n =  2'O-methyl modifications corresponding
      base
<220> FEATURE:
<221> NAME/KEY: misc_feature
<222> LOCATION: 20
<223> OTHER INFORMATION: n = thymidine phosphorothioate modification

<400> SEQUENCE: 114
ccuacugcag ggugaagaan t                                              21

<210> SEQ ID NO 115
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 6, 7, 8, 13, 16, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 115
gccacuucga aguagugcun t                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

-continued

```
<221> NAME/KEY: modified_base
<222> LOCATION: 6, 10, 12, 14, 15, 16
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 116
agagguggau augucugggn t                                              21

<210> SEQ ID NO 117
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 10, 12, 15, 17, 19
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 117
cuaacuggac acagugugun t                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 8, 11, 12, 13 14, 16, 17
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 118
agucggacag ccucaccaan t                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 5, 6, 7, 11, 12, 16, 17
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 119
gagcuuugga ucaaguuaan t                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 3, 5, 8, 10, 12, 13, 14, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 120
gacacagugu guuugauuun t                                              21

<210> SEQ ID NO 121
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 8, 10, 12, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 121
gaauggguuc acaaaucagn t                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 5, 7, 8, 9, 11, 12
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 122
auucuguuug uugaagggan t                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 7, 8, 9, 14, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 123
uaauucuuca cccugcagun t                                              21

<210> SEQ ID NO 124
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 6, 10, 12, 15, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 124
aaaaucaaac acacugugun t                                              21

<210> SEQ ID NO 125
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 4, 10, 12
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 125
ccauugggau auagggagcn t                                              21

<210> SEQ ID NO 126
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 7, 9, 12, 14, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 126
aucaaacaca cuguguccan t                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 8, 12, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 127
uuuuggucag augaucagan t                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 8, 15, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 128
agaaaaucaa gucgugcugn t                                               21

<210> SEQ ID NO 129
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 9, 11, 16, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 129
aguaauucuu cacccugcan t                                               21

<210> SEQ ID NO 130
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 6, 8, 11, 13, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 130
ucaaacacac uguguccagn t                                               21

<210> SEQ ID NO 131
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 6, 7, 8, 10, 11,
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 131
uucuguuugu ugaagggagn t                                               21

<210> SEQ ID NO 132
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 2, 5, 8, 10, 15, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 132
guaauucuuc acccugcagn t                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 7, 10, 13, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 133
uuugucuagu gcuuccaucn t                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 7, 11, 14, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 134
aaguggcaac ugaugagcan t                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 5, 8, 11, 15
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 135
cuaaugguga caacugaucn t                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

<221> NAME/KEY: modified_base
<222> LOCATION: 2, 7, 11, 13, 17
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 136
ucaacccaga cauauccacn t                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 8, 13, 15, 18
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 137
aauucuucac ccugcaguan t                                              21

<210> SEQ ID NO 138
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 4, 6, 11, 13, 16
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 138
uucuucaccc ugcaguaggn t                                              21

<210> SEQ ID NO 139
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6, 9, 16
<223> OTHER INFORMATION: n = 2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 139
agcacuacuu cgaaguggcn t                                              21

<210> SEQ ID NO 140
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:

```
<221> NAME/KEY: modified_base
<222> LOCATION: 3, 7, 9, 13
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 140
cccagacaua uccaccucun t                                              21

<210> SEQ ID NO 141
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 4, 7, 9, 13, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 141
acacacugug uccaguuagn t                                              21

<210> SEQ ID NO 142
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 11
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 142
uuggugaggc uguccgacun t                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 6, 7, 12
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 143
uuaacuugau ccaaagcucn t                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 5, 9, 11, 14, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 144
aaaucaaaca cacugugucn t                                               21

<210> SEQ ID NO 145
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 5, 6, 7, 9, 13, 14, 15, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 145
cugauuugug aacccauucn t                                               21

<210> SEQ ID NO 146
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 10, 14, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 146
ucccuucaac aaacagaaun t                                               21

<210> SEQ ID NO 147
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 10, 17, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 147
acugcagggu gaagaauuan t                                               21

<210> SEQ ID NO 148
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 2, 4, 7, 9, 11, 12, 13, 16, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 148
acacagugug uuugauuuun t                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 4, 5, 6, 7, 9, 11, 12, 13, 14, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 149
gcucccuaua ucccaauggn t                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 5, 7, 10, 12, 14, 15, 16, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 150
uggacacagu guguuugaun t                                              21

<210> SEQ ID NO 151
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 6, 7, 9, 10, 11, 14, 15
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 151
ucugaucauc ugaccaaaan t                                              21

<210> SEQ ID NO 152
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

<221> NAME/KEY: modified_base
<222> LOCATION: 1, 4, 6, 9, 10, 11,14, 15, 16, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 152
cagcacgacu ugauuuucun t                                              21

<210> SEQ ID NO 153
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 8, 15, 16, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 153
ugcaggguga agaauuacun t                                              21

<210> SEQ ID NO 154
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 6, 8, 11, 13, 15, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 154
cuggacacag uguguuugan t                                              21

<210> SEQ ID NO 155
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4,  5, 6, 7, 8, 11, 15
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 155
cucccuucaa caaacagaan t                                              21

<210> SEQ ID NO 156
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:

```
<221> NAME/KEY: modified_base
<222> LOCATION: 1, 2, 4, 9, 16, 17, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 156
cugcagggug aagaauuacn t                                          21

<210> SEQ ID NO 157
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 9, 11, 12, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 157
gauggaagca cuagacaaan t                                          21

<210> SEQ ID NO 158
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 5, 7, 8, 11, 12, 14, 15, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 158
ugcucaucag uugccacuun t                                          21

<210> SEQ ID NO 159
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 7, 8, 10, 11, 13, 14, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 159
gaucaguugu caccauuagn t                                          21

<210> SEQ ID NO 160
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 2, 6, 8, 10, 11, 12, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 160
guggauaugu cugguugan t                                               21

<210> SEQ ID NO 161
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 4, 6, 11, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 161
uacugcaggg ugaagaauun t                                              21

<210> SEQ ID NO 162
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 5, 6, 8, 13
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 162
ccuacugcag ggugaagaan t                                              21

<210> SEQ ID NO 163
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 3, 5, 6, 7, 8, 13, 16, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 163
gccacuucga aguagugcun t                                              21

<210> SEQ ID NO 164
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 6, 10, 12, 14, 15, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 164
agagguggau augucugggn t                                              21

<210> SEQ ID NO 165
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 5, 6, 10, 12, 15, 17, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 165
cuaacuggac acagugugun t                                              21

<210> SEQ ID NO 166
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 8, 11, 12, 13, 14, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 166
agucggacag ccucaccaan t                                              21

<210> SEQ ID NO 167
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 4, 5, 6, 7, 11, 12, 16, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 167
gagcuuugga ucaaguuaan t                                              21

<210> SEQ ID NO 168
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 3, 5, 8, 10, 12, 13, 14, 17, 18, 19
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 168
gacacagugu guuugauuun t                                              21

<210> SEQ ID NO 169
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 10, 12, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 169 gauggguuc acaaaucagn t                                               21

<210> SEQ ID NO 170
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 170
auucuguuug uugaagggan t                                              21

<210> SEQ ID NO 171
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1,9, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 171
uaauucuuca cccugcagun t                                              21

<210> SEQ ID NO 172
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 6, 10, 12
<223> OTHER INFORMATION: n =  2'O-methyl modification corresponding base
<220> FEATURE:
```

```
<221> NAME/KEY: misc_feature
<222> LOCATION: 20
<223> OTHER INFORMATION: n = thymidine phosphorothioate modification

<400> SEQUENCE: 172
aaaaucaaac acacugugun t                                              21

<210> SEQ ID NO 173
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 10, 12
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 173
ccauugggau auagggagcn t                                              21

<210> SEQ ID NO 174
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 7, 9, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 174
aucaaacaca cuguguccan t                                              21

<210> SEQ ID NO 175
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 8, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 175
uuuuggucag augaucagan t                                              21

<210> SEQ ID NO 176
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 8,
<223> OTHER INFORMATION: n =  2'O-methyl modification corresponding base
<220> FEATURE:
```

<221> NAME/KEY: misc_feature
<222> LOCATION: 20
<223> OTHER INFORMATION: n = thymidine phosphorothioate modification

<400> SEQUENCE: 176
agaaaaucaa gucgugcugn t                                            21

<210> SEQ ID NO 177
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 11, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 177
aguaauucuu cacccugcan t                                            21

<210> SEQ ID NO 178
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 6, 8, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 178
ucaaacacac uguguccagn t                                            21

<210> SEQ ID NO 179
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 179
uucuguuugu ugaagggagn t                                            21

<210> SEQ ID NO 180
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 10, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

```
<400> SEQUENCE: 180
guaauucuuc acccugcagn t                                              21

<210> SEQ ID NO 181
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 181
uuugucuagu gcuuccaucn t                                              21

<210> SEQ ID NO 182
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 7, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 182
aaguggcaac ugaugagcan t                                              21

<210> SEQ ID NO 183
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 11
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 183
cuaaugguga caacugaucn t                                              21

<210> SEQ ID NO 184
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 7, 11, 13, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification
```

```
<400> SEQUENCE: 184
ucaacccaga cauauccacn t                                        21

<210> SEQ ID NO 185
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 8, 15, 18
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 185
aauucuucac ccugcaguan t                                        21

<210> SEQ ID NO 186
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 6, 13, 16
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 186
uucuucaccc ugcaguaggn t                                        21

<210> SEQ ID NO 187
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 6
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 187
agcacuacuu cgaaguggcn t                                        21

<210> SEQ ID NO 188
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 7, 9, 13
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification
```

```
<400> SEQUENCE: 188
cccagacaua uccaccucun t                                              21

<210> SEQ ID NO 189
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 4, 13, 17
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 189
acacacugug uccaguuagn t                                              21

<210> SEQ ID NO 190
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = thymidine phosphorothioate modification

<400> SEQUENCE: 190
uuggugaggc uguccgacun t                                              21

<210> SEQ ID NO 191
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2,12
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 191
uuaacuugau ccaaagcucn t                                              21

<210> SEQ ID NO 192
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 5,9, 11
<223> OTHER INFORMATION: n =  2'O-methyl modification corresponding base
<220> FEATURE:
<221> NAME/KEY: misc_feature
<222> LOCATION: 20
<223> OTHER INFORMATION: n = thymidine phosphorothioate modification

<400> SEQUENCE: 192
aaaucaaaca cacugugucn t                                              21
```

RNAI MODULATION OF HIF-1 AND THERAPEUTIC USES THEREOF

RELATED APPLICATIONS

This application claims the benefit of U.S. Provisional Application No. 60/694,382, filed Jun. 27, 2005, which is incorporated herein by reference in its entirety.

SEQUENCE LISTING

This application incorporates by reference the sequence listing saved as an ASCII text file on CD-ROM. The sequence listing saved on CD-ROM was created on Oct. 2, 2006, and is identified as "14174-116001.txt." The file contains 70KB of data. Three identical copies of the sequence listing have been submitted, including one "Computer-Readable Format" (CRF) and two "Official Copies" (Copy 1 and Copy 2).

TECHNICAL FIELD

The invention relates to the field of HIF-1 targeted therapy and compositions and methods for modulating HIF-1α mRNA/protein levels by oligonucleotides via RNA interference which are administered locally to the eyes or systemically via injection/intravenous administration.

BACKGROUND

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function. RNAi has been suggested as a method of developing a new class of therapeutic agents. However, to date, these have remained mostly as suggestions with no demonstrate proof that RNAi can be used therapeutically.

Mammals require molecular oxygen for essential metabolic processes including oxidative phosphorylation in which oxygen serves as electron acceptor during ATP formation. Systemic, local, and intracellular homeostatic responses elicited by hypoxia (the state in which oxygen demand exceeds supply) include erythropoiesis by individuals who are anemic or at high altitude (Jelkmann (1992) Physiol. Rev. 72:449-489), neovascularization in ischemic myocardium (White et al. (1992) Circ. Res. 71:1490-1500), and glycolysis in cells cultured at reduced oxygen tension (Wolfle et al. (1983) Eur. J. Biochem. 135:405-412). These adaptive responses either increase oxygen delivery or activate alternate metabolic pathways that do not require oxygen. Hypoxia-inducible gene products that participate in these responses include erythropoietin (EPO) (reviewed in Semenza (1994) Hematol. Oncol. Clinics N. Amer. 8:863-884), vascular endothelial growth factor (Shweiki et al. (1992) Nature 359:843-845; Banai et al. (1994) Cardiovasc. Res. 28:1176-1179; Goldberg & Schneider (1994) J. Biol. Chem. 269:4355-4359), and glycolytic enzymes (Firth et al. (1994) Proc. Natl. Acad. Sci. USA 91:6496-6500; Semenza et al. (1994) J. Biol. Chem. 269: 23757-23763).

The molecular mechanisms that mediate genetic responses to hypoxia have been extensively investigated for the EPO gene, which encodes a growth factor that regulates erythropoiesis and thus blood oxygen carrying capacity (Jelkmann (1992) supra; Semenza (1994) supra). Cis-acting DNA sequences required for transcriptional activation in response to hypoxia were identified in the EPO 3'-flanking region and a trans-acting factor that binds to the enhancer, hypoxia-inducible factor 1 (HIF-1), fulfilled criteria for a physiological regulator of EPO transcription. Inducers of EPO expression (1% oxygen, cobalt chloride [$CoCl_2$], and desferrioxamine [DFX]) also induced HIF-1 DNA binding activity with similar kinetics; inhibitors of EPO expression (actinomycin D, cycloheximide, and 2-aminopurine) blocked induction of HIF-1 activity; and mutations in the EPO 3'-flanking region that eliminated HIF-1 binding also eliminated enhancer function (Semenza (1994) supra). These results also support the hypothesis that oxygen tension is sensed by a hemoprotein (Goldberg et al. (1988) Science 242:1412-1415) and that a signal transduction pathway requiring ongoing transcription, translation, and protein phosphorylation participates in the induction of HIF-1 DNA-binding activity and EPO transcription in hypoxic cells (Semenza (1994) supra).

EPO expression is cell type specific, but induction of HIF-1α activity by 1% oxygen, $CoCl_2$, or DFX was detected in many mammalian cell lines (Wang & Semenza (1993a) Proc. Natl. Acad. Sci. USA 90:4304-4308), and the EPO enhancer directed hypoxia-inducible transcription of reporter genes transfected into non-EPO-producing cells (Wang & Semenza (1993a) supra; Maxwell et al. (1993) Proc. Natl. Acad. Sci. USA 90:2423-2427). RNAs encoding several glycolytic enzymes were induced by 1% oxygen, $CoCl_2$, or DFX in EPO-producing Hep3B or non-producing HeLa cells whereas cycloheximide blocked their induction and glycolytic gene sequences containing HIF-1 binding sites mediated hypoxia-inducible transcription in transfection assays (Firth et al. (1994) supra; Semenza et al. (1994) supra). These experiments support the role of HIF-1 in activating homeostatic responses to hypoxia.

HIF-1 is a dimer composed of HIF-1α and HIF-1β subunits. While the HIF-1β subunit is constitutively expressed, the HIF-1α subunit is the limiting member of the heterodimer and therefore regulates HIF-1 levels. Under normoxic conditions, HIF-1α is ubiquinated and rapidly degraded. However, under hypoxic conditions the rate of ubiquitination dramatically decreases and HIF-1α is stabilized, resulting in upregulation of HIF-1 dimer. This is an important point and provides the rationale for targeting HIF-1α instead of HIF-1β for modulating HIF-1 activity.

Macular degeneration is a major cause of blindness in the United States and the frequency of this disorder increases with age. Macular degeneration refers to the group of diseases in which sight-sensing cells in the macular zone of the retina malfunction or loose function and which can result in debilitating loss of vital central or detail vision.

Age-related macular degeneration (AMD), which is the most common form of macular degeneration, occurs in two main forms. Ninety percent of people with AMD have the form described as "dry" macular degeneration. An area of the retina is affected, which leads to slow breakdown of cells in the macula, and a gradual loss of central vision. The other form of AMD is "wet" macular degeneration. Although only 10% of people with AMD have this type, it accounts for 90% of blindness from the disease. As dry AMD progresses, new blood vessels may begin to grow and cause "wet" AMD. These new blood vessels often leak blood and fluid under the macula. This causes rapid damage to the macula that can lead to loss of central vision in a short time. iRNA agents targeting HIF-1α can be useful for the treatment of wet and dry macular degeneration.

SUMMARY

The present invention is based on the in vitro demonstration that HIF-1α can be inhibited through local and systemic administration of iRNA agents, as well as by parenteral administration of such agents and the identification of potent iRNA agents from the HIF-1α gene that can reduce RNA levels and protein levels of HIF-1α in cells particularly in an organism. Based on these findings, the present invention provides specific compositions and methods that are useful in reducing HIF-1α mRNA levels and HIF-1α protein levels in a subject, e.g., a mammal, such as a human.

The present invention specifically provides iRNA agents consisting of, consisting essentially of or comprising at least 15 or more contiguous nucleotides of the HIF-1α gene and more particularly agents that comprising 15 or more contiguous nucleotides from one of the sequences provided in Tables 1, 2, 3, or 4. The iRNA agent preferably comprises less than 30 nucleotides per strand, e.g., 21-23 nucleotides, such as those provided in Tables 1, 2, 3, and 4. The double stranded iRNA agent can either have blunt ends or more preferably have overhangs of 1-4 nucleotides from one or both 3' ends of the agent.

Further, the iRNA agent can either contain only naturally occurring ribonucleotide subunits, or can be synthesized so as to contain one or more modifications to the sugar or base of one or more of the ribonucleotide subunits that is included in the agent. The iRNA agent can be further modified so as to be attached to a ligand that is selected to improve stability, distribution or cellular uptake of the agent, e.g. cholesterol. The iRNA agents can further be in isolated form or can be part of a pharmaceutical composition used for the methods described herein, particularly as a pharmaceutical composition formulated for delivery to the eye or formulated for parental administration. The pharmaceutical compositions can contain one or more iRNA agents, and in some embodiments, will contain two or more iRNA agents, each one directed to a different segment of a HIF-1α gene or a different HIF-1α gene.

The present invention further provides methods for reducing the level of HIF-1α protein and HIF-1α mRNA in a cell. Such methods comprise the step of administering one of the iRNA agents of the present invention to a subject as further described below. The present methods utilize the cellular mechanisms involved in RNA interference to selectively degrade the HIF-1α mRNA in a cell and are comprised of the step of contacting a cell with one of the HIF-1α iRNA agents of the present invention. Such methods can be performed directly on a cell or can be performed on a mammalian subject by administering to a subject one of the iRNA agents/pharmaceutical compositions of the present invention. Reduction of HIF-1α mRNA in a cell results in a reduction in the amount of HIF-1α protein produced, and in an organism (as shown in the Examples).

The methods and compositions of the invention, e.g., the methods and iRNA agent compositions can be used with any dosage and/or formulation described herein, as well as with any route of administration described herein. Particularly important is the showing herein of intraocular administration of an iRNA agent and its ability to inhibit HIF-1α protein in the eye.

In another aspect, the invention features a method for treating or preventing a disease or condition in a subject. The method can include administering to the subject a composition of the invention under conditions suitable for the treatment or prevention of the disease or condition in the subject, alone or in conjunction with one or more other therapeutic compounds.

In one embodiment, the iRNA agent is administered at or near the site of unwanted HIF-1α expression, e.g., direct injection at site, by a catheter or other placement device (e.g., a retinal pellet or an implant including a porous, non-porous, or gelatinous material). In one embodiment the iRNA agent is administered via an intraocular implant, which can be inserted, for example, into an anterior or posterior chamber of the eye; or into the sclera, transchoroidal space, or an avascularized region exterior to the vitreous. In another embodiment, the implant is positioned over an avascular region, such as on the sclera, so as to allow for transscleral diffusion of the drug to the desired site of treatment, e.g., to the intraocular space and macula of the eye. Furthermore, the site of transscleral diffusion is preferably in proximity to the macula.

In another embodiment, an iRNA agent is administered to the eye by injection, e.g., by intraocular, retinal, or subretinal injection.

In another embodiment, an iRNA agent is administered topically to the eye, such as by a patch or liquid eye drops, or by iontophoresis. Ointments or droppable liquids can be delivered by ocular delivery systems known in the art such as applicators or eye droppers.

In one embodiment, an iRNA is delivered at or near a site of neovascularization.

In one embodiment, an iRNA agent is administered repeatedly. Administration of an iRNA agent can be carried out over a range of time periods. It can be administered hourly, daily, once every few days, weekly, or monthly. The timing of administration can vary from patient to patient, depending upon such factors as the severity of a patient's symptoms. For example, an effective dose of an iRNA agent can be administered to a patient once a month for an indefinite period of time, or until the patient no longer requires therapy. In addition, sustained release compositions containing an iRNA agent can be used to maintain a relatively constant dosage in the area of the target HIF-1α nucleotide sequences.

In another embodiment, an iRNA agent is delivered to the eye at a dosage on the order of about 0.00001 mg to about 3 mg per eye, or preferably about 0.000°-0.001 mg per eye, about 0.03-3.0 mg per eye, about 0.1-3.0 mg per eye or about 0.3-3.0 mg per eye.

In another embodiment, an iRNA agent is administered prophylactically such as to prevent or slow the onset of a disorder or condition that affects the eye. For example, an iRNA can be administered to a patient who is susceptible to or otherwise at risk for a neovascular disorder.

In one embodiment one eye of a human is treated with an iRNA agent described herein, and in another embodiment, both eyes of a human are treated.

In another aspect, a method of inhibiting HIF-1α expression is provided. One such method includes administering an effective amount of an iRNA agent including sense and antisense sequences capable of forming an RNA duplex. The sense sequence of the iRNA agent can include a nucleotide sequence substantially identical to a target sequence of about 19 to 23 nucleotides of HIF-1α mRNA, and the antisense sequence can include a nucleotide sequence complementary to a target sequence of about 19-23 nucleotides of HIF-1α.

In another aspect, a method of treating adult onset macular degeneration is provided. One such method includes administering a therapeutically effective amount of an iRNA agent that includes sense and antisense sequences capable of forming an RNA duplex. The sense sequence can include a nucleotide sequence substantially identical to a target sequence of about 19 to 23 nucleotides of HIF-1α mRNA. The antisense sequence can include a nucleotide sequence complementary to a target sequence of about 19 to 23 nucleotides of HIF-1α mRNA.

In one embodiment, a human has been diagnosed with dry age-related macular degeneration (AMD), and in another embodiment the human has been diagnosed with wet AMD.

In one embodiment, a human treated with an iRNA agent described herein is over the age of 50, e.g., between the ages of 75 and 80, and the human has been diagnosed with age-related macular degeneration. In another embodiment, a human treated with an iRNA agent described herein is between the ages of 30-50, and the human has been diagnosed with late onset macular degeneration. In another embodiment, a human treated with an iRNA agent described herein is between the ages of 5-20, and the human has been diagnosed with middle onset macular degeneration. In another embodiment, a human treated with an iRNA agent described herein is 7 years old or younger, and the human has been diagnosed with early onset macular degeneration.

In one aspect, methods of treating any disease or disorder characterized by unwanted HIF-1α expression are provided. Particularly preferred embodiments include the treatment of disorders of the eye or retina, which are characterized by unwanted HIF-1α expression. The disease or disorder can be a diabetic retinopathy, neovascular glaucoma, a tumor or metastatic cancer (e.g., colon or breast cancer), a pulmonary disease (e.g., asthma or bronchitis), rheumatoid arthritis, or psoriasis. Other angiogenic disorders can be treated by the methods featured in the invention.

In another aspect, the invention features a kit containing an iRNA agent of the invention. The iRNA agent of the kit can be chemically modified and can be useful for modulating the expression of a HIF-1α target gene in a cell, tissue or organism. In one embodiment, the kit contains more than one iRNA agent of the invention.

The details of one or more embodiments of the invention are set forth in the accompanying drawings and the description below. Other features, objects, and advantages of the invention will be apparent from this description, the drawings, and from the claims. This application incorporates all cited references, patents, and patent applications by references in their entirety for all purposes.

BRIEF DESCRIPTION OF DRAWINGS

FIGS. 3A-3F: A spreadsheet (Table 5) shows HIF-1α mRNA levels determined by the bDNA assays described in Example 2. A corresponding graph is shown in FIG. 1.

DETAILED DESCRIPTION

Figure 1:
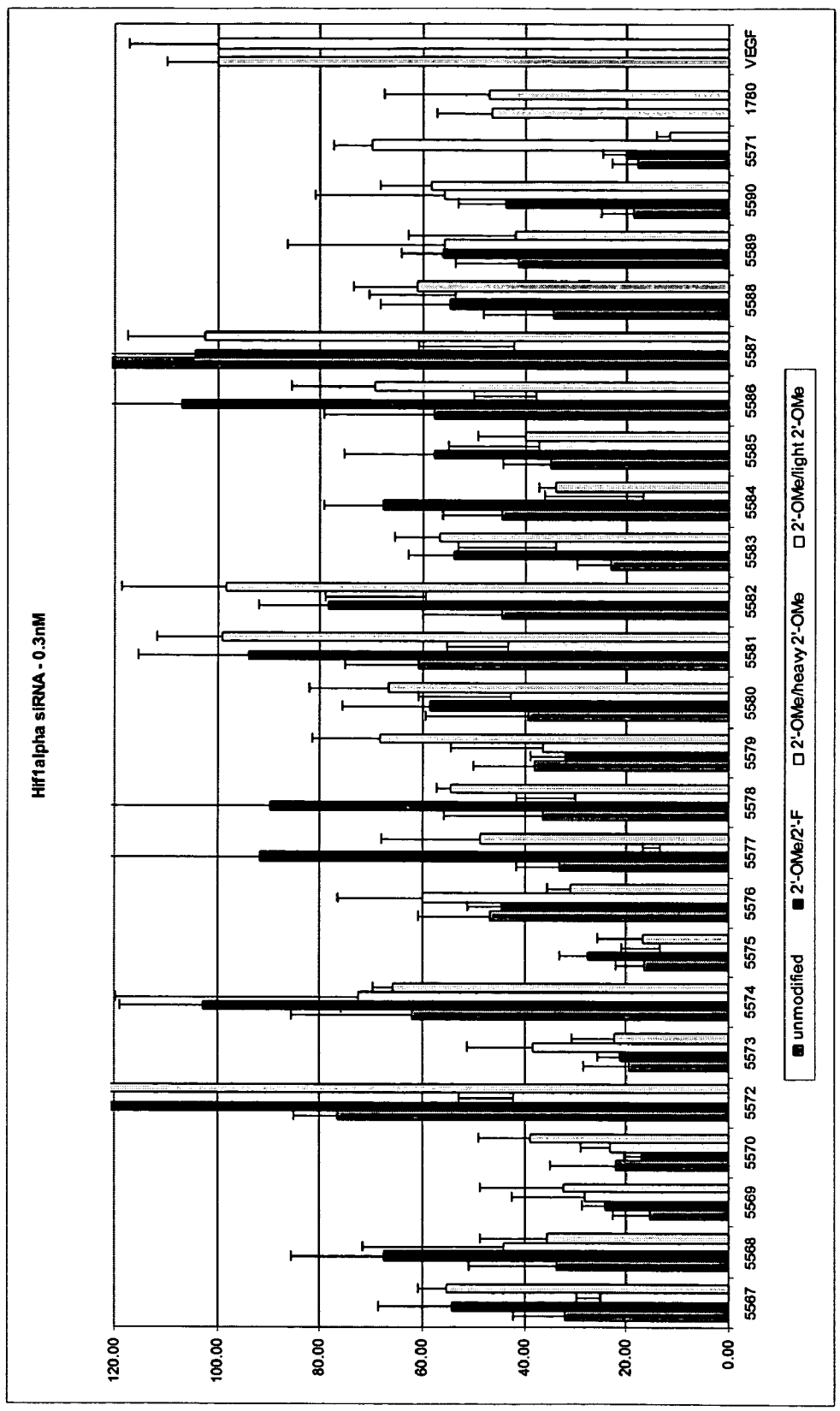
FIG. 1: In vitro inhibition of HIF-1α using iRNA agents. iRNA agents provided in Tables 1, 2, 3, and 4 were tested for anti-HIF-1α activity as described in the Examples. Each column (bar) represents an iRNA agent provided in Tables 1, 2, 3, and 4, e.g. column 1 is the first agent in Table 1, column 2 is the first agent in Table 2, column 3 is the first agent in Table 3, and column 4 is the first agent in Table 4. The y-axis on the graph represents percent target HIF-1α mRNA as compared to the amount of target mRNA in untreated cells. The corresponding data is shown in Table 5 (FIG. 3). Active iRNA agents were identified by causing a decrease in the quantity of target HIF-1α mRNA.

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, all of which are described herein or are well known in the RNA synthetic art. While numerous modified RNAs and nucleoside surrogates are described, preferred examples include those which have greater resistance to nuclease degradation than do unmodified RNAs. Examples include those that have a 2' sugar modification, a modification in a single strand overhang, such as a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can down-regulate the expression of a target gene, e.g., HIF-1α. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded (ds) iRNA agent.

A "ds iRNA agent" (abbreviation for "double stranded iRNA agent"), as used herein, is an iRNA agent which includes more than one, and preferably two, strands in which interchain hybridization can form a region of duplex structure. A "strand" herein refers to a contiguous sequence of nucleotides (including non-naturally occurring or modified nucleotides). The two or more strands may be, or each form a part of, separate molecules, or they may be covalently interconnected, e.g. by a linker, e.g. a polyethylene glycol linker, to form but one molecule. At least one strand can include a region which is sufficiently complementary to a target RNA. Such strand is termed the "antisense strand". A second strand comprised in the dsRNA agent that comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host. The iRNA agents of the present invention include molecules which are sufficiently short that they do not trigger a deleterious interferon response in mammalian cells. Thus, the administration of a composition of an iRNA agent (e.g., formulated as described herein) to a mammalian cell can be used to silence expression of an HIF-1α gene while circumventing a deleterious interferon response. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 60 but preferably less than 50, 40, or 30 nucleotide pairs.

The isolated iRNA agents described herein, including ds iRNA agents and siRNA agents, can mediate silencing of a gene, e.g., by RNA degradation. For convenience, such RNA is also referred to herein as the RNA to be silenced. Such a gene is also referred to as a target gene. Preferably, the RNA to be silenced is a gene product of an HIF-1α gene.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secrete at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

As used herein, the term "complementary" is used to indicate a sufficient degree of complementarity such that stable and specific binding occurs between a compound of the invention and a target RNA molecule, e.g. an HIF-1α mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target HIF-1α mRNA) if the iRNA agent reduces the production of a protein encoded by the target RNA in a cell. The iRNA agent may also be "exactly complementary" to the target RNA, e.g., the target RNA and the iRNA agent anneal, preferably to form a hybrid made exclusively of Watson-Crick base pairs in the region of exact complementarity. A "sufficiently complementary" iRNA agent can include an internal region (e.g., of at least 10 nucleotides) that is exactly complementary to a target HIF-1α RNA. Moreover, in some embodiments, the iRNA agent specifically discriminates a single-nucleotide difference. In this case, the iRNA agent only mediates RNAi if exact complementarity is found in the region (e.g., within 7 nucleotides of) the single-nucleotide difference. Preferred iRNA agents will be based on or consist or comprise the sense and antisense sequences provided in the Examples.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil).

As used herein, a "subject" refers to a mammalian organism undergoing treatment for a disorder mediated by HIF-1α expression, such as undergoing treatment prophylactically or therapeutically to prevent HIF-1α production. The subject can be any mammal, such as a primate, cow, horse, mouse, rat, dog, pig, goat. In the preferred embodiment, the subject is a human.

As used herein, treating a disorder mediated by HIF-1α refers to the amelioration of any biological or pathological endpoints that 1) is mediated in part by the unwanted expression or over expression of HIF-1α in the subject and 2) whose outcome can be affected by reducing the level of HIF-1α gene products present.

Design and Selection of iRNA agents

The present invention is based on the demonstration of target gene silencing of the HIF-1α gene in vivo following local administration an iRNA agent results in reducing biological and pathological processes mediated, at least in part by, HIF-1α expression.

Based on these results, the invention specifically provides an iRNA agent that can be used in reducing HIF-1α levels in a cell or organism, particularly for use in reducing unwanted HIF-1α expression, in isolated form and as a pharmaceutical composition described below. Such agents will include a sense strand having at least 15 or more contiguous nucleotides that are complementary to a HIF-1α gene and an antisense strand having at least 15 or more contiguous nucleotides that are complementary to the sense strand sequence. Particularly useful are iRNA agents that comprise a nucleotide sequence from the HIF-1α as provided in Tables 1, 2, 3, and 4.

Other candidate iRNA agents can be designed by performing, for example, a gene walk analysis of the HIF-1α gene that will serve as the iRNA target. Overlapping, adjacent, or closely spaced candidate agents corresponding to all or some of the transcribed region can be generated and tested. Each of the iRNA agents can be tested and evaluated for the ability to down regulate the target gene expression (see below, "Evaluation of Candidate iRNA agents").

Preferably, the iRNA agents of the present invention are based on and comprise at least 15 or more contiguous nucleotides from one of the iRNA agents shown to be active in Tables 1, 2, 3, and 4. In such agents, the agent can comprise the entire sequence provided in the table or can comprise 15 or more contiguous residues along with additional nucleotides from contiguous regions of the target gene.

An iRNA agent can be rationally designed based on sequence information and desired characteristics and the information provided in Tables 1, 2, 3, and 4. For example, an iRNA agent can be designed according to the relative melting temperature of the candidate duplex. Generally, the duplex should have a lower melting temperature at the 5' end of the antisense strand than at the 3' end of the antisense strand.

Accordingly, the present invention provides iRNA agents comprising a sense strand and antisense strand each comprising a sequence of at least 15, 16, 17, 18, 19, 20, 21 or 23 nucleotides which is essentially identical to, as defined above, a portion of the HIF-1α gene. Exemplified iRNA agents include those that comprise 15 or more contiguous nucleotides from one of the agents provided in Tables 1, 2, 3, and 4.

The antisense strand of an iRNA agent should be equal to or at least, 15, 16, 17, 18, 19, 25, 29, 40, or 50 nucleotides in length. It should be equal to or less than 50, 40, or 30, nucleotides in length. Preferred ranges are 15-30, 17 to 25, 19 to 23, and 19 to 21 nucleotides in length. Exemplified iRNA agents include those that comprise 15 or more nucleotides from one of the agents in Tables 1, 2, 3, and 4.

The sense strand of an iRNA agent should be equal to or at least 15, 16 17, 18, 19, 25, 29, 40, or 50 nucleotides in length. It should be equal to or less than 50, 40, or 30 nucleotides in length. Preferred ranges are 15-30, 17 to 25, 19 to 23, and 19 to 21 nucleotides in length. Exemplified iRNA agents include those that comprise 15 or more nucleotides from one of the agents in Tables 1, 2, 3, and 4.

The double stranded portion of an iRNA agent should be equal to or at least, 15, 16 17, 18, 19, 20, 21, 22, 23, 24, 25, 29, 40, or 50 nucleotide pairs in length. It should be equal to or less than 50, 40, or 30 nucleotides pairs in length. Preferred ranges are 15-30, 17 to 25, 19 to 23, and 19 to 21 nucleotides pairs in length.

The agents provided in Tables 1, 2, 3, and 4 are 21 nucleotides in length for each strand. The iRNA agents contain a 19 nucleotide double stranded region with a 2 nucleotide overhang on each of the 3' ends of the agent. These agents can be modified as described herein to obtain equivalent agents comprising at least a portion of these sequences (15 or more contiguous nucleotides) and or modifications to the oligonucleotide bases and linkages.

Generally, the iRNA agents of the instant invention include a region of sufficient complementarity to the HIF-1α gene, and are of sufficient length in terms of nucleotides, that the iRNA agent, or a fragment thereof, can mediate down regulation of the specific HIF-1α gene. The antisense strands of the iRNA agents of the present invention are preferably fully complementary to the mRNA sequences of HIF-1α gene. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an HIF-1α mRNA.

Therefore, the iRNA agents of the instant invention include agents comprising a sense strand and antisense strand each comprising a sequence of at least 16, 17 or 18 nucleotides which is essentially identical, as defined below, to one of the sequences of a HIF-1α gene such as those agent provided in Tables 1, 2, 3, and 4, except that not more than 1, 2 or 3 nucleotides per strand, respectively, have been substituted by other nucleotides (e.g. adenosine replaced by uracil), while essentially retaining the ability to inhibit HIF-1α expression in cultured human cells, as defined below. These agents will therefore possess at least 15 or more nucleotides identical to one of the sequences of a HIF-1α gene but 1, 2 or 3 base mismatches with respect to either the target HIF-1α mRNA sequence or between the sense and antisense strand are introduced. Mismatches to the target HIF-1α mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule, such as those exemplified in Tables 1, 2, 3, and 4. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length, on one or both ends of the iRNA agent. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the siRNA agent range discussed above. Embodiments in which the two strands of the siRNA agent are linked, e.g., covalently linked are also included. Hairpin, or other single strand structures which provide the required double stranded region, and preferably a 3' overhang are also within the invention.

Evaluation of Candidate iRNA Agents

A candidate iRNA agent can be evaluated for its ability to down regulate target gene expression. For example, a candidate iRNA agent can be provided, and contacted with a cell, e.g. a human cell that expresses HIF-1α. Alternatively, the cell can be transfected with a construct from which a target HIF-1α gene is expressed, thus preventing the need for endogenous HIF-1α expression. The level of target gene expression prior to and following contact with the candidate iRNA agent can be compared, e.g. on an mRNA or protein level. If it is determined that the amount of RNA or protein expressed from the target gene is lower following contact with the iRNA agent, then it can be concluded that the iRNA agent down-regulates target gene expression. The level of target HIF-1α mRNA or HIF-1α protein in the cell or tissue can be determined by any method desired. For example, the level of target RNA can be determined by Northern blot analysis, reverse transcription coupled with polymerase chain reaction (RT-PCR), bDNA analysis, or RNAse protection assay. The level of protein can be determined, for example, by Western blot analysis or immuno-fluorescence.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability. Tables 1, 2, 3, and 4 provides a variety of sequence modifications as exemplars.

In Vivo Testing

An iRNA agent identified as being capable of inhibiting HIF-1α gene expression can be tested for functionality in vivo in an animal model (e.g., in a mammal, such as in mouse or rat) as shown in the examples. For example, the iRNA agent can be administered to an animal, and the iRNA agent evaluated with respect to its biodistribution, stability, and its ability to inhibit HIF-1α, e.g. lower HIF-1α protein or gene expression.

The iRNA agent can be administered directly to the target tissue, such as by injection, or the iRNA agent can be administered to the animal model in the same manner that it would be administered to a human.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}S$, $^{32}P$, $^{33}P$, or $^{3}H$; gold particles; or antigen particles for immunohistochemistry).

The iRNA agent can be evaluated with respect to its ability to down regulate HIF-1α gene expression. Levels of HIF-1α gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target HIF-1α mRNA can be detected by any desired method, including but not limited to RT-PCR, Northern blot, branched-DNA assay, or RNAase protection assay. Alternatively, or additionally, HIF-1α gene expression can be monitored by performing Western blot analysis on tissue extracts treated with the iRNA agent.

iRNA Chemistry

Described herein are isolated iRNA agents, e.g., ds RNA agents, that mediate RNAi to inhibit expression of a HIF-1α gene.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets HIF-1α, can have enhanced resistance to nucleases.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R═H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-AMINE and aminoalkoxy, O(CH$_2$)$_n$AMINE, (e.g., AMINE=NH$_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-OCH3,2'-O-allyl, 2'-C-allyl, and 2'-fluoro.

One way to increase resistance is to identify cleavage sites and modify such sites to inhibit cleavage, as described in co-owned U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization are preferably used only in terminal regions, and more preferably not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Delivery of iRNA Agents to Tissues and Cells

Formulation

The iRNA agents described herein can be formulated for administration to a subject, preferably for administration locally to eyes, or parenterally, e.g. via injection.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences. In another embodiment, each iRNA agents is directed to a different gene, e.g. VEGF.

Treatment Methods and Routes of Delivery

A composition that includes an iRNA agent of the present invention, e.g., an iRNA agent that targets HIF-1α, can be delivered to a subject by a variety of routes. Exemplary routes include inhalation, intrathecal, parenchymal, intravenous, nasal, oral, and ocular delivery. The preferred means of administering the iRNA agents of the present invention is through direct administration to the eye or systemically through parental administration.

An iRNA agent can be incorporated into pharmaceutical compositions suitable for administration. For example, compositions can include one or more iRNA agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal, intrapulmonary), oral or parenteral. Parenteral administration includes intravenous drip, subcutaneous, intraperitoneal or intramuscular injection, or intrathecal or intraventricular administration.

In general, the delivery of the iRNA agents of the present invention is done to achieve delivery into the subject to the site of infection. The preferred means of achieving this is through either a local administration to the eye, or via systemic administration, e.g. parental administration.

Formulations for direct injection and parenteral administration are well known in the art. Such formulation may include sterile aqueous solutions which may also contain buffers, diluents and other suitable additives. For intravenous use, the total concentration of solutes should be controlled to render the preparation isotonic.

Administration of the iRNA Agents A patient who has been diagnosed with a disorder characterized by unwanted HIF-1α expression can be treated by administration of an iRNA agent described herein to block the negative effects of HIF-1α, thereby alleviating the symptoms associated with unwanted HIF-1α gene expression. For example, the iRNA agent can alleviate symptoms associated with a disease of the eye, such as a neovascular disorder. In other examples, the iRNA agent can be administered to treat a patient who has a tumor or metastatic cancer, such as colon or breast cancer; a pulmonary disease, such as asthma or bronchitis; or an autoimmune disease such as rheumatoid arthritis or psoriasis. The anti-HIF-1α iRNA agents can be administered systemically, e.g., orally or by intramuscular injection or by intravenous injection, in admixture with a pharmaceutically acceptable carrier adapted for the route of administration. An iRNA agent can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., *Trends in Cell Bio.* 2:139, 1992; *Delivery Strategies for Antisense Oligonucleotide Therapeutics*, ed. Akhtar, 1995; Maurer et al., *Mol. Membr. Biol.*, 16:129, 1999; Hofland and Huang, *Handb. Exp. Pharmacol.* 137:165, 1999; and Lee et al., *ACS Symp. Ser.* 752:184, 2000, all of which are incorporated herein by reference. Beigelman et al., U.S. Pat. No. 6,395,713 and Sullivan et al., PCT WO 94/02595 further describe the general methods for delivery of nucleic acid molecules. Nucleic acid molecules can be administered to cells by a variety of methods known to those of skill in the art, including, but not restricted to, encapsulation in liposomes, by ionophoresis, or by incorporation into other vehicles, such as hydrogels, cyclodextrins (see for example Gonzalez et al., *Bioconjugate Chem.* 10:1068, 1999), biodegradable nanocapsules, and bioadhesive microspheres, or by proteinaceous vectors (O'Hare and Normand, International PCT Publication No. WO 00/53722).

In the present methods, the iRNA agent can be administered to the subject either as naked iRNA agent, in conjunction with a delivery reagent, or as a recombinant plasmid or viral vector which expresses the iRNA agent. Preferably, the iRNA agent is administered as naked iRNA.

The iRNA agent of the invention can be administered to the subject by any means suitable for delivering the iRNA agent to the cells of the tissue at or near the area of unwanted HIF-1α expression, such as at or near an area of neovascularization. For example, the iRNA agent can be administered by gene gun, electroporation, or by other suitable parenteral administration routes.

Suitable enteral administration routes include oral delivery.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intra-retinal injection, or sub-retinal injection); subcutaneous injection or deposition including subcutaneous infusion (such as by osmotic pumps); direct application to the area at or near the site of neovascularization, for example by a catheter or other placement device (e.g., a retinal pellet or an implant comprising a porous, non-porous, or gelatinous material). It is preferred that injections or infusions of the iRNA agent be given at or near the site of neovascularization.

The iRNA agent of the invention can be delivered using an intraocular implant. Such implants can be biodegradable and/or biocompatible implants, or may be non-biodegradable implants. The implants may be permeable or impermeable to the active agent, and may be inserted into a chamber of the eye, such as the anterior or posterior chambers, or may be implanted in the sclera, transchoroidal space, or an avascularized region exterior to the vitreous. In a preferred embodiment, the implant may be positioned over an avascular region, such as on the sclera, so as to allow for transscleral diffusion of the drug to the desired site of treatment, e.g., the intraocular space and macula of the eye. Furthermore, the site of transscleral diffusion is preferably in proximity to the macula.

The iRNA agent of the invention can also be administered topically, for example, by patch or by direct application to the eye, or by iontophoresis. Ointments, sprays, or droppable liquids can be delivered by ocular delivery systems known in the art such as applicators or eyedroppers. The compositions can be administered directly to the surface of the eye or to the interior of the eyelid. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

The iRNA agent of the invention may be provided in sustained release compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

An iRNA agent can be injected into the interior of the eye, such as with a needle or other delivery device.

The iRNA agent of the invention can be administered in a single dose or in multiple doses. Where the administration of the iRNA agent of the invention is by infusion, the infusion can be a single sustained dose or can be delivered by multiple infusions. Injection of the agent directly into the tissue is at or near the site of neovascularization is preferred. Multiple injections of the agent into the tissue at or near the site of neovascularization are also preferred.

Dosage levels on the order of about 1 μg/kg to 100 mg/kg of body weight per administration are useful in the treatment of the neovascular diseases. When administered directly to the eye, the preferred dosage range is about 0.00001 mg to about 3 mg per eye, or preferably about 0.0001-0.001 mg per eye, about 0.03-3.0 mg per eye, about 0.1-3.0 mg per eye or about 0.3-3.0 mg per eye. One skilled in the art can also readily determine an appropriate dosage regimen for administering the iRNA agent of the invention to a given subject. For example, the iRNA agent can be administered to the subject once, e.g., as a single injection or deposition at or near the neovascularization site. Alternatively, the iRNA agent can be administered once or twice daily to a subject for a period of from about three to about twenty-eight days, more preferably from about seven to about ten days. In a preferred dosage regimen, the iRNA agent is injected at or near a site of unwanted HIF-1 expression (such as near a site of neovascularization) once a day for seven days. Where a dosage regimen comprises multiple administrations, it is understood that the effective amount of iRNA agent administered to the subject can comprise the total amount of iRNA agent administered over the entire dosage regimen. One skilled in the art will appreciate that the exact individual dosages may be adjusted somewhat depending on a variety of factors, including the specific iRNA agent being administered, the time of administration, the route of administration, the nature of the formulation, the rate of excretion, the particular disorder being treated, the severity of the disorder, the pharmacodynamics of the iRNA agent, and the age, sex, weight, and general health of the patient. Wide variations in the necessary dosage level are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known in the art. The precise therapeutically effective dosage levels and patterns are preferably determined by the attending physician in consideration of the above-identified factors.

In addition to treating pre-existing neovascular diseases, iRNA agents of the invention can be administered prophylactically in order to prevent or slow the onset of these and related disorders. In prophylactic applications, an iRNA of the invention is administered to a patient susceptible to or otherwise at risk of a particular neovascular disorder.

The iRNA agents featured by the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science*, 18th ed., Mack Publishing Company, Easton, Pa. (1990), and *The Science and Practice of Pharmacy*, 2003, Gennaro et al., the entire disclosures of which are herein incorporated by reference.

The present pharmaceutical formulations comprise an iRNA agent of the invention (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more iRNA agents of the invention.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as PluronicP85), which can enhance entry of drugs into the CNS (Jolliet-Riant and Tillement, *Fundam. Clin. Pharmacol.* 13:16, 1999); biodegradable polymers, such as poly (DL-lactide-coglycolide) microspheres for sustained release delivery. Other non-limiting examples of delivery strategies for the nucleic acid molecules of the instant invention include material described in Boado et al., *J. Pharm. Sci.* 87:1308, 1998; Tyler et al., *FEBS Lett.* 421:280, 1999; Pardridge et al., *PNAS USA.* 92:5592, 1995; Boado, *Adv. Drug Delivery Rev.* 15:73, 1995; Aldrian-Herrada et al., *Nucleic Acids Res.* 26:4910, 1998; and Tyler et al., *PNAS USA* 96:7053, 1999.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., *Chem. Rev.* 95:2601, 1995; Ishiwata et al., *Chem. Phare. Bull.* 43:1005, 1995).

Such liposomes have been shown to accumulate selectively in tumors, presumably by extravasation and capture in the neovascularized target tissues (Lasic et al., *Science* 267:1275, 1995; Oku et al., *Biochim. Biophys. Acta* 1238:86, 1995). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 42:24864, 1995; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain iRNA agents of the instant invention can be expressed within cells from eukaryotic promoters (e.g., Izant and Weintraub, *Science* 229:345, 1985; McGarry and Lindquist, *Proc. Natl. Acad. Sci. USA* 83:399, 1986; Scanlon et al., *Proc. Natl. Acad. Sci. USA* 88:10591, 1991; Kashani-Sabet et al., *Antisense Res. Dev.* 2:3, 1992; Dropulic et al., *J. Virol.* 66:1432, 1992; Weerasinghe et al., *J. Virol.* 65:5531, 1991; Ojwang et al., *Proc. Natl. Acad. Sci. USA* 89:10802, 1992; Chen et al., *Nucleic Acids Res.* 20:4581, 1992; Sarver et al., *Science* 247:1222, 1990; Thompson et al., *Nucleic Acids Res.* 23:2259, 1995; Good et al., *Gene Therapy* 4:45, 1997). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., *Nucleic Acids Symp. Ser.* 27:156, 1992; Taira et al., *Nucleic Acids Res.* 19:5125, 1991; Ventura et al., *Nucleic Acids Res.* 21:3249, 1993; Chowrira et al., *J. Biol. Chem.* 269:25856, 1994).

In another aspect of the invention, RNA molecules of the present invention can be expressed from transcription units (see for example Couture et al., *Trends in Genetics* 12:510, 1996) inserted into DNA or RNA vectors. The recombinant vectors can be DNA plasmids or viral vectors. iRNA agent-expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pats. Nos. 5,902,880 and 6,146,886). The recombinant vectors capable of expressing the iRNA agents can be delivered as described above, and persist in target cells. Alternatively, viral vectors can be used that provide for transient expression of nucleic acid molecules. Such vectors can be repeatedly administered as necessary. Once expressed, the iRNA agent interacts with the target mRNA and generates an RNAi response. Delivery of iRNA agent-expressing vectors can be systemic, such as by intravenous or intra-muscular administration, by administration to target cells ex-planted from a subject followed by reintroduction into the subject, or by any other means that would allow for introduction into the desired target cell (for a review see Couture et al., *Trends in Genetics* 12:510, 1996).

Additional ophthalmic indications for the iRNA agents of the invention include proliferative diabetic retinopathy (the most severe stage of diabetic retinopathy), uveitis (an inflammatory condition of the eye that often leads to macular edema), cystoid macular edema following cataract surgery, myopic degeneration (a condition in which a patient with a high degree of nearsightedness develops choroidal neovascularization), inflammatory macular degeneration (a condition in which a patient with inflammation in the macular area due to infections or other causes, develops choroidal neovascularization), and iris neovascularization (a serious complication of diabetic retinopathy or retinal vein occlusion involving new blood vessel growth on the surface of the iris).

Additional non-ophthalmic indications for the iRNA agents of the invention include cancer, including but not limited to renal and colon cancer, and psoriasis. Solid tumors and their metastases rely on new blood vessel growth for their survival.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the subject with no significant adverse toxicological effects on the subject.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage. An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of iRNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of iRNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Because iRNA agent mediated silencing can persist for several days after administering the iRNA agent composition, in many instances, it is possible to administer the composition with a frequency of less than once per day, or, for some instances, only once for the entire therapeutic regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracistemal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. direct administration to the eye. For example, eye formulations tend to require much lower concentrations of some ingredients in order to avoid irritation or burning of the ocular tissues. It is sometimes desirable to dilute an oral formulation up to 10-100 times in order to provide a suitable ocular formulation.

Certain factors may influence the dosage required to effectively treat a subject, including but not limited to the severity of the disease or disorder, previous treatments, the general health and/or age of the subject, and other diseases present. It will also be appreciated that the effective dosage of an iRNA agent such as an siRNA agent used for treatment may increase or decrease over the course of a particular treatment. Changes in dosage may result and become apparent from the results of diagnostic assays. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models.

The invention is further illustrated by the following examples, which should not be construed as further limiting.

EXAMPLES

Example 1

Figure 2:
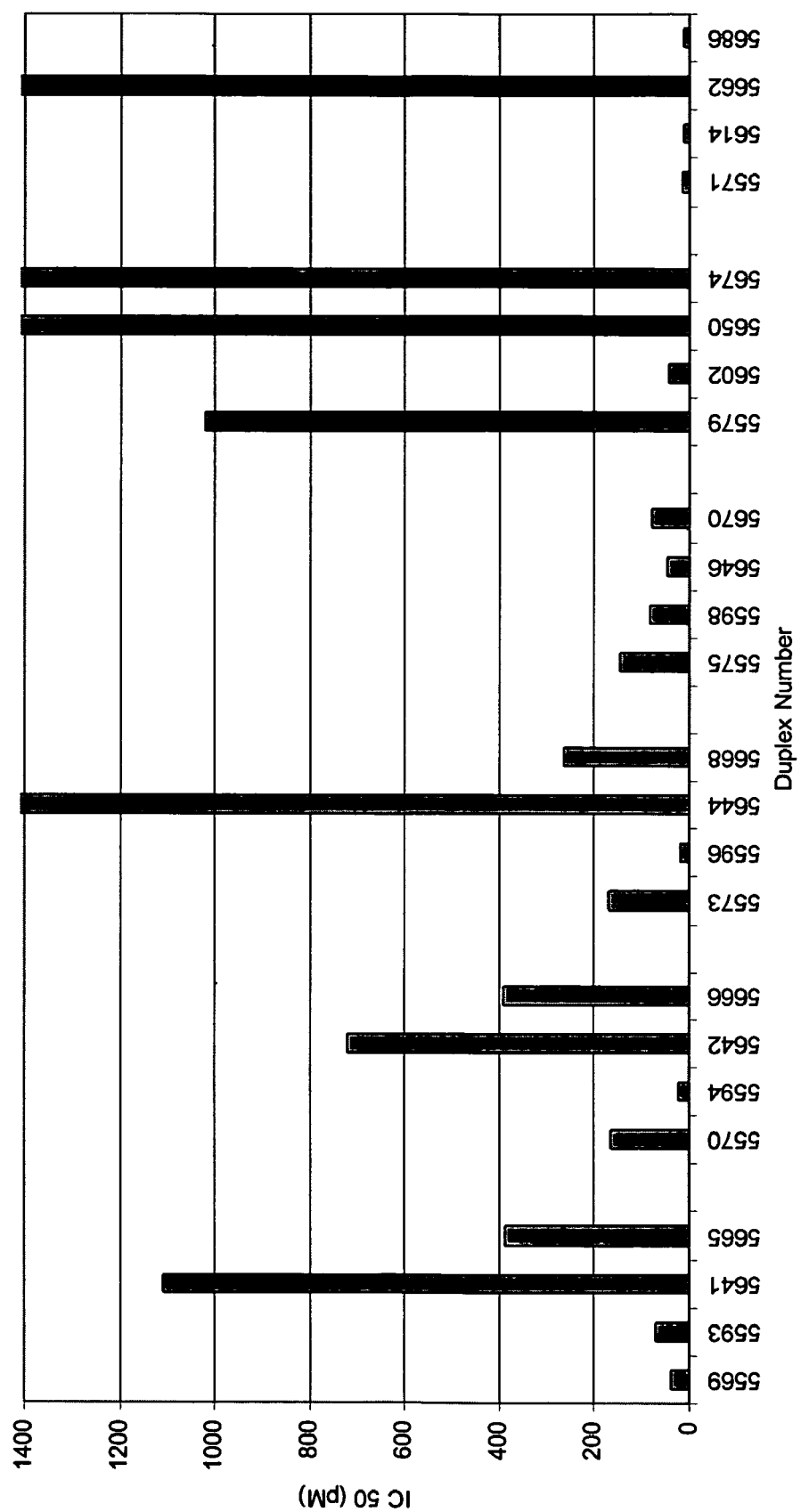
FIG. 2 shows the IC50 of candidate anti-HIF-1α siRNAs as determined by Elisa assay. In vitro dose response inhibition of HIF-1α using iRNA agents was performed as described in the Examples. Active agents from Tables 1, 2, 3, and 4 were tested. A dose dependent response was observed.

Designing Anti-HIF-1α siRNAs Against HIF-1α mRNA siRNA against HIF-1α mRNA were synthesized chemically using known procedures. The siRNA sequences and some inhibition and IC50 values are listed (see Tables 1, 2, 3 and 4, and FIG. 2). Four different groups of siRNAs were synthesized and tested. The first group, listed in Table 1, were unmodified, except for a few exceptions that included a phosphorothioate modification. The second, third and fourth group, listed in Tables 2, 3 and 4, respectively, included phosphorothioate modifications, 2'0-methyl modifications and 2'-fluoro modifications. Modifications in the oligonucleotide strands were accomplished by using the appropriate modified monomer phosphoramidite as described in detail above.

TABLE 1

HIF-1alpha siRNAs

| oligo name | sense strand sequence (5'-3') | SEQ ID NO: | oligo name | antisense strand sequence (5'-3') | SEQ ID NO: | duplex name |
|---|---|---|---|---|---|---|
| AL6070 | CUGAUUUGUGAACCCAUUCTT | 1 | AL6071 | GAAUGGGUUCACAAAUCAGTT | 25 | AL-DP-5567 |
| AL6072 | UCCCUUCAACAAACAGAAUTT | 2 | AL6073 | AUUCUGUUUGUUGAAGGGATT | 26 | AL-DP-5568 |
| AL6074 | ACUGCAGGGUGAAGAAUUATsT | 3 | AL6075 | UAAUUCUUCACCCUGCAGUTsT | 27 | AL-DP-5569 |
| AL6076 | ACACAGUGUGUUUGAUUUUTsT | 4 | AL6077 | AAAAUCAAACACACUGUGUTsT | 28 | AL-DP-5570 |
| AL6078 | GCUCCCUAUAUCCCAAUGGTT | 5 | AL6079 | CCAUUGGGAUAUAGGGAGCTT | 29 | AL-DP-5572 |
| AL6080 | UGGACACAGUGUGUUUGAUTsT | 6 | AL6081 | AUCAAACACACUGUGUCCATsT | 30 | AL-DP-5573 |
| AL6082 | UCUGAUCAUCUGACCAAAATT | 7 | AL6083 | UUUUGGUCAGAUGAUCAGATT | 31 | AL-DP-5574 |
| AL6084 | CAGCACGACUUGAUUUUCUTsT | 8 | AL6085 | AGAAAAUCAAGUCGUGCUGTsT | 32 | AL-DP-5575 |
| AL6086 | UGCAGGGUGAAGAAUUACUTT | 9 | AL6087 | AGUAAUUCUUCACCCUGCATT | 33 | AL-DP-5576 |
| AL6088 | CUGGACACAGUGUGUUUGATT | 10 | AL6089 | UCAAACACACUGUGUCCAGTT | 34 | AL-DP-5577 |
| AL6090 | CUCCCUUCAACAAACAGAATT | 11 | AL6091 | UUCUGUUUGUUGAAGGGAGTT | 35 | AL-DP-5578 |
| AL6092 | CUGCAGGGUGAAGAAUUACTsT | 12 | AL6093 | GUAAUUCUUCACCCUGCAGTsT | 36 | AL-DP-5579 |
| AL6094 | GAUGGAAGCACUAGACAAATT | 13 | AL6095 | UUUGUCUAGUGCUUCCAUCTT | 37 | AL-DP-5580 |
| AL6096 | UGCUCAUCAGUUGCCACUUTT | 14 | AL6097 | AAGUGGCAACUGAUGAGCATT | 38 | AL-DP-5581 |
| AL6098 | GAUCAGUUGUCACCAUUAGTT | 15 | AL6099 | CUAAUGGUGACAACUGAUCTT | 39 | AL-DP-5582 |

TABLE 1-continued

HIF-1alpha siRNAs

| oligo name | sense strand sequence (5'-3') | SEQ ID NO: | oligo name | antisense strand sequence (5'-3') | SEQ ID NO: | duplex name |
|---|---|---|---|---|---|---|
| AL6100 | GUGGAUAUGUCUGGGUUGATT | 16 | AL6101 | UCAACCCAGACAUAUCCACTT | 40 | AL-DP-5583 |
| AL6102 | UACUGCAGGGUGAAGAAUUTT | 17 | AL6103 | AAUUCUUCACCCUGCAGUATT | 41 | AL-DP-5584 |
| AL6104 | CCUACUGCAGGGUGAAGAATT | 18 | AL6105 | UUCUUCACCCUGCAGUAGGTT | 42 | AL-DP-5585 |
| AL6106 | GCCACUUCGAAGUAGUGCUTT | 19 | AL6107 | AGCACUACUUCGAAGUGGCTT | 43 | AL-DP-5586 |
| AL6108 | AGAGGUGGAUAUGUCUGGGTT | 20 | AL6109 | CCCAGACAUAUCCACCUCUTT | 44 | AL-DP-5587 |
| AL6110 | CUAACUGGACACAGUGUGUTT | 21 | AL6111 | ACACACUGUGUCCAGUUAGTT | 45 | AL-DP-5588 |
| AL6112 | AGUCGGACAGCCUCACCAATT | 22 | AL6113 | UUGGUGAGGCUGUCCGACUTT | 46 | AL-DP-5589 |
| AL6114 | GAGCUUUGGAUCAAGUUAATT | 23 | AL6115 | UUAACUUGAUCCAAAGCUCTT | 47 | AL-DP-5590 |
| AL6116 | GACACAGUGUGUUUGAUUUTsT | 24 | AL6117 | AAAUCAAACACACUGUGUCTsT | 48 | AL-DP-5571 | s: Phosphothioate double overhang design

TABLE 2

HIF-1alpha siRNAs: modified 1

| oligo name | SEQ ID NO: | sense strand sequence (5'-3') | oligo name | SEQ ID NO: | antisense strand sequence (5'-3') |
|---|---|---|---|---|---|
| AL6120 | 49 | cuGAuuuGuGAAcccAuucTsT | AL6121 | 73 | GAAuGGGuucAcAAAucAGTsT |
| AL6122 | 50 | ucccuucAAcAAAcAGAAuTsT | AL6123 | 74 | AuucuGuuuGuuGAAGGGATsT |
| AL6124 | 51 | ACuGcAGGGuGAAGAAuuATsT | AL6125 | 75 | uAAuucuucAcccuGcAGuTsT |
| AL6126 | 52 | AcAcAGuGuGuuuGAuuuuTsT | AL6127 | 76 | AAAAucAAAcAcAcuGuGuTsT |
| AL6128 | 53 | GcucccuAuAucccAAuGGTsT | AL6129 | 77 | ccAuuGGGAuAuAGGGAGcTsT |
| AL6130 | 54 | uGGAcAcAGuGuGuuuGAuTsT | AL6131 | 78 | AucAAAcAcAcuGuGuccATsT |
| AL6132 | 55 | ucuGAucAucuGAccAAAATsT | AL6133 | 79 | uuuuGGucAGAuGAucAGATsT |
| AL6134 | 56 | cAGcAcGAcuuGAuuuucuTsT | AL6135 | 80 | AGAAAAucAAGucGuGcuGTsT |
| AL6136 | 57 | uGCAGGGuGAAGAAuuAcuTsT | AL6137 | 81 | AGuAAuucuucAcccuGcATsT |
| AL6138 | 58 | cuGGAcACAGuGuGuuuGATsT | AL6139 | 82 | ucAAAcAcAcuGuGuccAGTsT |
| AL6140 | 59 | cucccuucAAcAAAcAGAATsT | AL6141 | 83 | uucuGuuuGuuGAAGGGAGTsT |
| AL6142 | 60 | cuGcAGGGuGAAGAAuuAcTsT | AL6143 | 84 | GuAAuucuucAcccuGcAGTsT |
| AL6144 | 61 | GAuGGAAGcAcuAGAcAAATsT | AL6145 | 85 | uuuGucuAGuGcuuccAucTsT |
| AL6146 | 62 | uGcucAucAGuuGccAcuuTsT | AL6147 | 86 | AAGuGGcAAcuGAuGAGcATsT |
| AL6148 | 63 | GAucAGuuGucAccAuuAGTsT | AL6149 | 87 | cuAAuGGuGAcAAcuGAucTsT |
| AL6150 | 64 | GuGGAuAuGucuGGGuuGATsT | AL6151 | 88 | ucAAcccAGAcAuAuccAcTsT |
| AL6152 | 65 | uAcuGcAGGGuGAAGAAuuTsT | AL6153 | 89 | AAuucuucAcccuGcAGuATsT |
| AL6154 | 66 | ccuAcuGcAGGGuGAAGAATsT | AL6155 | 90 | uucuucAcccuGcAGuAGGTsT |
| AL6156 | 67 | GccAcuucGAAGuAGuGcuTsT | AL6157 | 91 | AGcAcuAcuucGAAGuGGcTsT |
| AL6158 | 68 | AGAGGuGGAuAuGucuGGGTsT | AL6159 | 92 | cccAGAcAuAuccAcccucuTsT |
| AL6160 | 69 | cuAAcuGGAcAcAGuGuGuTsT | AL6161 | 93 | AcAcAcuGuGuccAGuuAGTsT |
| AL6162 | 70 | AGucGGAcAGccucAccAATsT | AL6163 | 94 | uuGGuGAGGcuGuccGAcuTsT |

TABLE 2-continued

HIF-1alpha siRNAs: modified 1

| oligo name | SEQ ID NO: | sense strand sequence (5'-3') | oligo name | SEQ ID NO: | antisense strand sequence (5'-3') |
|---|---|---|---|---|---|
| AL6164 | 71 | GAGcuuuGGAucAAGuuAATsT | AL6165 | 95 | uuAAcuuGAuccAAAGcucTsT |
| AL6166 | 72 | GAcAcAGuGuCuuuGAuuuTsT | AL6167 | 96 | AAAucAAAcAcAcuGuGucTsT | s: Phosphothioate; lower case letter is a 2'OMe modified base; underlined letter is a 2'F base double overhang design

TABLE 3

HIF-1alpha siRNAs: modified 2

| oligo name | sense strand sequence (5'-3') | SEQ ID NO: | oligo name | antisense strand sequence (5'-3') | SEQ ID NO: | duplex name |
|---|---|---|---|---|---|---|
| AL6120 | cuGAuuuGuGAAcccAuucTsT | 97 | AL6324 | GAAuGGGuUcAcAAAUcAGTsT | 121 | AL-DP-5639 |
| AL6122 | ucccuucAAcAAAcAGAAuTsT | 98 | AL6325 | AuUCuGuuuGuuGAAGGGAuTsT | 122 | AL-DP-5640 |
| AL6124 | AcuGcAGGGuGAAGAAuuATsT | 99 | AL6326 | uAAuUCuUcACCCuGcAGUTsT | 123 | AL-DP-5641 |
| AL6126 | AcAcAGuGuGuuuGAuuuuTsT | 100 | AL6327 | AAAAUcAAAcAcACuGuGUTsT | 124 | AL-DP-5642 |
| AL6128 | GcucccuAuAucccAAuGGTsT | 101 | AL6328 | CcAuUGGGAuAuAGGGAGCTsT | 125 | AL-DP-5643 |
| AL6130 | uGGAcAcAGuGuGuuuGAuTsT | 102 | AL6329 | AUcAAAcAcACuGuGuUCcATsT | 126 | AL-DP-5644 |
| AL6132 | ucuGAucAucuGAccAAAATsT | 103 | AL6330 | uUuuGGUcAGAuGAUcAGATsT | 127 | AL-DP-5645 |
| AL6134 | cAGcAcGAcuuGAuuuucuTsT | 104 | AL6331 | AGAAAAUcAAGUCGuGCuGTsT | 128 | AL-DP-5646 |
| AL6136 | uGcAGGGuGAAGAAuuAcuTsT | 105 | AL6332 | AGuAAuUCuUcACCCuGcATsT | 129 | AL-DP-5647 |
| AL6138 | cuGGAcAcAGuGuGuuuGATsT | 106 | AL6333 | UcAAAcAcACuGuGUGcAGTsT | 130 | AL-DP-5648 |
| AL6140 | cucccuucAAcAAAcAGAATsT | 107 | AL6334 | uUCuGuuuGuuGAAGGGAGTsT | 131 | AL-DP-5649 |
| AL6142 | cuGcAGGGuGAAGAAuuAcTsT | 108 | AL6335 | GuAAuUCuUcACCCuGcAGTsT | 132 | AL-DP-5650 |
| AL6144 | GAuGGAAGcAcuAGAcAAATsT | 109 | AL6336 | uuuGUCuAGuGCuUCcAUGTsT | 133 | AL-DP-5651 |
| AL6146 | uGcucAucAGuuGccAcuuTsT | 110 | AL6337 | AAGuGGcAACuGAuGAGcATsT | 134 | AL-DP-5652 |
| AL6148 | GAucAGuuGucAccAuuAGTsT | 111 | AL6338 | CuAAuGGuGAcAACuGAUCTsT | 135 | AL-DP-5653 |
| AL6150 | GuGGAuAuGucuGGGuuGATsT | 112 | AL6339 | UcAACCcAGAcAuAUCcACTsT | 136 | AL-DP-5654 |
| AL6152 | uAcuGcAGGGuGAAGAAuuTsT | 113 | AL6340 | AAuUCuUcACCCuGcAGuATsT | 137 | AL-DP-5655 |
| AL6154 | ccuAcuGcAGGGuGAAGAATsT | 114 | AL6341 | uUCuUcACCCuGcAGuAGGTsT | 138 | AL-DP-5656 |
| AL6156 | GccAcuucGAAGuAGuGcuTsT | 115 | AL6342 | AGcACuAcUUCGAAGuGGCTsT | 139 | AL-DP-5657 |
| AL6158 | AGAGGuGGAuAuGucuGGGTsT | 116 | AL6343 | CCcAGAcAuAUCcACCUCUTsT | 140 | AL-DP-5658 |
| AL6160 | cuAAcuGGAcAcAGuGuGuTsT | 117 | AL6344 | AcAcACuGuGUCcAGuuAGTsT | 141 | AL-DP-5659 |
| AL6162 | AGucGGAcAGccucAccAATsT | 118 | AL6345 | uuGGuGAGGCuGUCCGACUTsT | 142 | AL-DP-5660 |
| AL6164 | GAGcuuuGGAucAAGuuAATsT | 119 | AL6346 | uuAACuuGAUCcAAAGCUCTsT | 143 | AL-DP-5661 |
| AL6166 | GAcAcAGuGuGuuuGAuuuTsT | 120 | AL6347 | AAAUcAAAcAcACuGuGUCTsT | 144 | AL-DP-5662 | s: Phosphothioate; lower case letter is a 2'OMe modified base; underlined letter is a 2'F base

TABLE 4

HIF-1alpha siRNAs: modified 3

| | | SEQ ID NO: | | | SEQ ID NO: | |
|---|---|---|---|---|---|---|
| AL6120 | cuGAuuuGuGAAcccAuucTsT | 145 | AL6348 | GAAUGGGUUcAcAAAUcAGTsT | 169 | AL-DP-5663 |
| AL6122 | UcccuucAAcAAAcAGAAuTsT | 146 | AL6349 | AUUCUGUUUGUUGAAGGGAUsT | 170 | AL-DP-5664 |
| AL6124 | AcUGcAGGGUGAAGAAUUATsT | 147 | AL6350 | uAAUUCUUcACCCUGcAGUTsT | 171 | AL-DP-5665 |
| AL6126 | AcAcAGuGUGUuUGAUuuuTsT | 148 | AL6351 | AAAAUcAAAcAcACUGUGUTsT | 172 | AL-DP-5666 |
| AL6128 | GcUcccUAUAUcccAAUGGTsT | 149 | AL6352 | CcAUUGGGAuAuAGGGAGCTsT | 173 | AL-DP-5667 |
| AL6130 | UGGAcAcAGUGUGUUuGAuTsT | 150 | AL6353 | AUcAAAcAcACUGUGUCcATsT | 174 | AL-DP-5668 |
| AL6132 | UcUGAUcAUcUGAccAAAATsT | 151 | AL6354 | UUUUGGUcAGAUGAUcAGATsT | 175 | AL-DP-5669 |
| AL6134 | cAGcAcGAcuuGAuuuucuTsT | 152 | AL6355 | AGAAAAUcAAGUCGUGCUGTsT | 176 | AL-DP-5670 |
| AL6136 | uGcAGGGuGAAGAAUUAcuTsT | 153 | AL6356 | AGuAAUUCUUcACCCUGcATsT | 177 | AL-DP-5671 |
| AL6138 | cUGGAcAcAGUGUGUUUGATsT | 154 | AL6357 | UcAAAcAcACUGUGUCcAGTsT | 178 | AL-DP-5672 |
| AL6140 | cucccuucAAcAAAcAGAATsT | 155 | AL6358 | UUCUGUUUGUUGAAGGGAGTsT | 179 | AL-DP-5673 |
| AL6142 | cuGcAGGGuGAAGAAuuAcTsT | 156 | AL6359 | GuAAUUCUUcACCCUGcAGTsT | 180 | AL-DP-5674 |
| AL6144 | GAuGGAAGcAcuAGAcAAATsT | 157 | AL6360 | UUUGUCuAGUGCUUCcAUCTsT | 181 | AL-DP-5675 |
| AL6146 | uGcucAucAGuuGccAcuuTsT | 158 | AL6361 | AAGUGGcAACUGAUGAGcATsT | 182 | AL-DP-5676 |
| AL6148 | GAucAGuuGucAccAuuAGTsT | 159 | AL6362 | CuAAUGGUGAcAACUGAUCTsT | 183 | AL-DP-5677 |
| AL6150 | GuGGAuAuGucuGGGuuGATsT | 160 | AL6363 | UcAACCcAGAcAuAUCcACTsT | 184 | AL-DP-5678 |
| AL6152 | uAcuGcAGGGuGAAGAAuuTsT | 161 | AL6364 | AAUUCUUcACCCUGcAGuATsT | 185 | AL-DP-5679 |
| AL6154 | ccuAcuGcAGGGuGAAGAATsT | 162 | AL6365 | UUCUUcACCCUGcAGuAGGTsT | 186 | AL-DP-5680 |
| AL6156 | GccAcuucGAAGuAGuGcuTsT | 163 | AL6366 | AGcACuACUUCGAAGUGGCTsT | 187 | AL-DP-5681 |
| AL6158 | AGAGGuGGAuAuGucuGGGTsT | 164 | AL6367 | CCcAGAcAuAUCcACCUCUTsT | 188 | AL-DP-5682 |
| AL6160 | cuAAcuGGAcAcAGuGuGuTsT | 165 | AL6368 | AcAcACUGUGUCcAGUuAGTsT | 189 | AL-DP-5683 |
| AL6162 | AGucGGAcAGccucAccAATsT | 166 | AL6369 | UUGGUGAGGCUGUCCGACUTsT | 190 | AL-DP-5684 |
| AL6164 | GAGcuuuGGAucAAGuuAATsT | 167 | AL6370 | UuAACUUGAUCcAAAGCUCTsT | 191 | AL-DP-5685 |
| AL6166 | GAcAcAGuGuGuuuGAuuuTsT | 168 | AL6371 | AAAUcAAAcAcACUGUGUCTsT | 192 | AL-DP-5686 | s: Phosphothioate; lower case letter is a 2'OMe modified base; underlined letter is a 2'F base double overhang design Example 2

HIF-1α siRNA In Vitro Screening Protocol

HeLa cells were grown at 37° C. in Dulbecco's modified Eagle medium (DMEM) supplemented with 10% fetal bovine serum (FBS), 100 units/mL penicillin, and 100 μg/mL streptomycin. Twenty-four hours prior to siRNA transfection, cells were seeded on 96-well plates at a concentration of 10,000 cells/well in antibiotic-free, DMEM. Cells were then transfected with HIF-1α targeting siRNAs at a concentration of 0.3 nM using Oligofectamine (Invitrogen). After 24 h, HIF-1α mRNA levels were determined in cell lysates using the bDNA assay (Genospectra). GAPDH mRNA levels were used to normalize the HIF-1α mRNA levels. Gene silencing mediated by each HIF-1α targeting siRNA was represented relative to an unrelated control siRNA. Data is shown in Table 5 (FIG. 3).

What is claimed is:

1. A method of reducing the levels of a HIF-1α protein or HIF-1α mRNA in a cell in a subject comprising the step of administering an iRNA agent to said subject, wherein the iRNA agent comprises a sense strand and an antisense strand having at least 15 or more contiguous nucleotides complementary to a mammalian HIF-1α target sequence, and wherein the target sequence differs by no more than 1, 2, or 3 nucleotides from SEQ ID NO:8.

2. The method of claim 1, wherein said iRNA agent is administered intraocularly to a subject.

3. A method of inhibiting HIF-1α expression comprising administering an effective amount of an iRNA agent, wherein the iRNA agent comprises a sense strand and an antisense strand having at least 15 or more contiguous nucleotides complementary to a mammalian HIF-1α target sequence, and wherein the target sequence differs by no more than 1, 2, or 3 nucleotides from SEQ ID NO:8.

4. The method of claim 1, wherein the sense and antisense strands of the iRNA agent form an RNA duplex, and wherein the antisense strand comprises a nucleotide sequence sufficiently complementary to a target sequence of about 19 to 23 nucleotides of a HIF-1α nucleotide sequence and wherein the target sequence differs by no more than 1, 2, or 3 nucleotides from SEQ ID NO:8.

5. The method of claim 1, wherein the sense strand comprises a sequence that differs by no more than 1, 2, or 3 nucleotides from SEQ ID NO:8.

6. The method of claim 1, wherein the iRNA agent further comprises a non-nucleotide moiety.

7. The method of claim 1, wherein the sense and antisense strands are stabilized against nucleolytic degradation.

8. The method of claim 1, wherein the sense and antisense strands form an RNA duplex, and the duplex comprises one 3'-overhang wherein said 3'-overhang comprises from 1 to 6 nucleotides.

9. The method of claim 8, wherein the duplex further comprises a second 3'-overhang wherein said second 3'-overhang comprises from 1 to 6 nucleotides.

10. The method of claim 1, wherein the iRNA agent comprises a phosphorothioate at the first internucleotide linkage at the 5' end of the antisense and sense strands.

11. The method of claim 1, wherein the iRNA agent comprises a phosphorothioate at the first internucleotide linkage at the 3' end of the antisense and sense strands.

12. The method of claim 1, wherein the iRNA agent comprises a phosphorothioate at the first internucleotide linkage at the 5' end of the antisense and sense strands, and a phosphorothioate at the first internucleotide linkage at the 3' end of the antisense and sense strands.

13. The method of claim 1, wherein the iRNA agent comprises a 2'-modified nucleotide.

14. The method of claim 13, wherein the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O- dimethylaminoethyl (2'-O-DMAOE), 2'-O-dimethylaminopropyl (2'-O-DMAP), 2'-O-dimethylaminoethyloxyethyl (2'-O-DMAEOE), and 2'-O-N-methylacetamido (2'-O-NMA).

15. The method of claim 1, wherein the sense and antisense strands form an RNA duplex, and the region of complementarity between the sense and antisense strands is 19 to 21 nucleotide pairs in length.

16. The method of claim 1, wherein the antisense strand comprises a sequence that differs by no more than 1, 2, or 3 nucleotides from SEQ ID NO:32.

17. The method of claim 1, wherein the sense strand comprises 19-23 nucleotides of SEQ ID NO:8.

18. The method of claim 1, wherein the sense strand consists of SEQ ID NO:8 and the antisense strand consists of SEQ ID NO:32.

19. The method of claim 2, wherein the sense strand comprises 19-23 nucleotides of SEQ ID NO:8.

20. The method of claim 2, wherein the sense strand consists of SEQ ID NO:8 and the antisense strand consists of SEQ ID NO:32.

21. The method of claim 3, wherein the sense strand comprises 19-23 nucleotides of SEQ ID NO:8.

22. The method of claim 3, wherein the sense strand consists of SEQ ID NO:8 and the antisense strand consists of SEQ ID NO:32.

23. The method of claim 3, wherein the method comprises inhibiting HIF-1α expression in vitro, wherein the sense strand consists of SEQ ID NO:8 and the antisense strand consists of SEQ ID NO:32.

24. The method of claim 3, wherein the method comprises inhibiting expression of HIF-1α in vivo comprising administration of the iRNA to target cells in the eye, and wherein the sense strand consists of SEQ ID NO:8 and the antisense strand consists of SEQ ID NO:32.

25. The method of claim 1 or 3, wherein the sense strand consists of SEQ ID NO:56 and the antisense strand consists of SEQ ID NO:80.

26. The method of claim 1 or 3, wherein the sense strand consists of SEQ ID NO:104 and the antisense strand consists of SEQ ID NO:128.

27. The method of claim 1 or 3, wherein the sense strand consists of SEQ ID NO:152 and the antisense strand consists of SEQ ID NO:176.

* * * * *